(12) United States Patent
Giroux et al.

(10) Patent No.: US 7,425,669 B2
(45) Date of Patent: Sep. 16, 2008

(54) TRANSGENIC PLANTS EXPRESSING PUROINDOLINES AND METHODS FOR PRODUCING SUCH PLANTS

(75) Inventors: Michael J. Giroux, Bozeman, MT (US); John Sherwood, Bozeman, MT (US); Krishnamurthy Konduru, Rockville, MD (US); Craig F. Morris, Pullman, WA (US)

(73) Assignees: The United States of America as represented by the Secretary of Agriculture, Washington, DC (US); Montana State University, Bozeman, MT (US)

( * ) Notice: Subject to any disclaimer, the term of this patent is extended or adjusted under 35 U.S.C. 154(b) by 607 days.

(21) Appl. No.: 10/447,541

(22) Filed: May 27, 2003

(65) Prior Publication Data

US 2003/0200561 A1    Oct. 23, 2003

Related U.S. Application Data

(60) Division of application No. 09/489,674, filed on Jan. 24, 2000, now Pat. No. 6,600,090, which is a continuation-in-part of application No. 09/083,852, filed on May 22, 1998, now Pat. No. 6,596,930.

(51) Int. Cl.
*A01H 5/00* (2006.01)
*A01H 1/00* (2006.01)
*C12N 15/82* (2006.01)

(52) U.S. Cl. .................... 800/301; 800/317.4; 800/320; 800/279; 800/266

(58) Field of Classification Search ................. 435/419, 435/411; 800/298, 301, 320, 279, 317.4
See application file for complete search history.

(56) References Cited

U.S. PATENT DOCUMENTS

| | | | |
|---|---|---|---|
| 5,187,073 A | 2/1993 | Goldman et al. | |
| 5,500,361 A | 3/1996 | Kinney | |

OTHER PUBLICATIONS

Beecher et al., "Expression of Wild-Type *pinB* Sequence in Transgenic Wheat Complements a Hard Phenotype," *Theor Appl. Genet.* 105:870-877 (2002).

Blochet, J.E., A. Kaboulou, J.-P. Compoint, and D. Marion, "Amphiphilic Proteins from Wheat Flour: Specific Extraction, Structure and Lipid Binding Properties," *In Glutenin Proteins 1990*, W. Bushul and R. Thachuk (eds.), American Association of Cereal Chemists, St. Paul, MN. p. 314-325 (1991).

Blochet J.E., C. Chevalier, E. Forest, E. Pebay-Peyroula, M.-F. Gautier, P. Joudrier, M. Pézolet, and D. Marion, "Complete Amino Acid Sequence of Puroindoline, a New Basic and Cystine-rich Protein with a Unique Tryptophan-rich Domain, Isolated from Wheat Endosperm by Triton X114 Phase Partitioning," *FEBS Lett* 329:336-340 (1993).

Bowie et al. "Deciphering the message in protein sequences: tolerance to amino acid substitutions," *Science* vol. 247.

Broun et al., Catalytic plasticity of fatty acid modification enzymes underlying chemical diversity of plant lipids,: *Science* 282:13 (1998).

Cheng, M. et al., "Genetic Transformation of Wheat Mediated by *Agrobacterium tumefaciens*," *Plant Physiol.* 115:971-980 (1997).

Chevreau et al., "Transformation of Apple for Durable Scab Resistance Expression of a Puroindoline Gene in Susceptible and Resistant (Vf) Genotypes," *Prov. IV IS on In Vitro Cult. & Hort. Breeding*, S. Sorvari et al. (eds) p. 232-326 (2001).

Dubrieil, L., Gaborit, T., Bouchet, B. Gallant, D.J., Broekaert, W.F., Quillien, L., and Marion, D., "Spatial and temporal distribution of the major isoforms of puroindolines (puriondoline-a and puroindoline-b) and non specific lipid transfer protein (ns-LTPel) of *Triticum aestivum* seeds. Relationships with their in vitro antifungal properties," *Plant Science* 138:121-135 (1998).

Gautier, M.F., M.-E. Aleman, A. Guirao, D. Marion, and P. Joudrier, "*Triticum aestivum* Puroindolines, Two Basic Cystine-rich Seed Proteins: cDNA Sequence Analysis and Developmental Gene Expression," *Plant Molecular Biology* 25:43-57 (1994).

Giroux, M.J. and C.F. Morris, "A Glycine to Serine Change in Puroindoline b Is Associated with Wheat Grain Hardness and Low Levels of Starch-surface Friabilin," *Theoretical and Applied Genetics*, 95:857-864 (Oct. 1997).

Giroux, M.J. and Morris, C.F. "Wheat grain hardness results from highly conserved mutations in the friablin components puroindoline a and b," *Proc. Natl. Acad. Sci.* 95:6262-6266 (1998).

Napoli, C. et al., "Introduction of a Chimeric Chalone Synthase Gene into Petunia Results in Reversible Co-Suppression of Homologous Genes in trans," *The Plant Cell* 2:279-289 (1990).

Prado, V.F., Lee, C.H., Zahed, L., Vekemans, M. and Nishioka, Y., "Molecular Characterization of a mouse Y chromosomal repetitive sequence that detects transcripts in the testis," *Cytogenet. Cell Genet.* 61(2): 87-90 (1992).

Rao, "Antimicrobal Peptides 6," *Molecular Plant-Microbe Interactions* 8(1):6-13 (1995).

Rahman, S. Jolly, C.J., Skerritt, J.H. and Wallosheck, "A. Cloning of a wheat 15-kDa grain softness protein (GSP). GSP is a mixtrure of puroindoline-like polypeptides," *Eur. J. Biochem.* 223:(3)917-925 (1994).

Tanchak, M., Schernthaner, J.P., Giband, M., and Altosaar I., "Tryptophanins: isolation and molecular characterization of oat cDNA clones encoding proteins structurally related to puroindoline and wheat grain softness proteins," *Plant Science* 137:173-184 (1998).

(Continued)

*Primary Examiner*—Anne Kubelik
(74) *Attorney, Agent, or Firm*—Howard V. Owens; Margaret A. Connor; John D. Fado

(57) ABSTRACT

The invention relates to plant cells, plant tissues or plants transgenic for a nucleic acid encoding puroindoline A. This invention also relates to methods for producing such transgenic plant cells, plant tissues or plants. The transgenic plants produced by the methods of this invention are useful in reducing the damage caused by plant pests, especially plant pathogens such as fungi and bacteria.

23 Claims, No Drawings

OTHER PUBLICATIONS

Van Der Krol, A. et al., "inhibition of Flower Pigmentation by Antisense CHS Gens: Promoter and Minimal Sequence Requirements for the Antisense Effect," *Plant Molecular Biology* 14:457-466 (1990).

Wilde, P.J., D.C. Clark, and D. Marion, "Influence of Competitive Adsorption of Lysopalmitoyl Phosphatidylcholine on the Functional Properties of Puroindoline, a Lipid Binding Protein Isolated from Wheat Flour," *J. Agric. Food Chem.* 41:1570-1576(1993).

Database Genbank, NCBI, Accession No. X69912, Gautier et al. (1994).

Database Genbank, NCBI, Accession No. X69913, Gautier et al. (1994).

Database Genbank, NCBI, Accession No. X69914, Gautier et al. (1994).

Database Genbank, NCBI, Accession No. S46515, Prado et al. (1993).

Database Genbank, NCBI, Accession No. X80378, Rahman et al. (1994).

Database Genbank, NCBI, Accession No. X80379, Rahman et al (1994).

Database Genbank, NCBI, Accession No. X80380, Rahman et al (1994).

Database Genbank, NCBI, Accession No. X80381, Rahman et al (1994).

Database Genbank, NCBI, Accession No. S72696, Rahman et al (1994).

Giroux, M.J., Talbert, L., Habernicht, D.K., Lanning, S., Hemphill, A., and Martin, J.M., "Association of Puriondoline Sequence Type and Grain Hardness in Hard Red Spring Wheat," *Crop Science* 40/2: 370-374 (2000).

Greenblatt, G.A., A.D. Bettge, and C.F. Morris, "Relationship Between Endosperm Texture and the Occurrence of Friabilin and Bound Polar Lipids on Wheat Starch," *Cereal Chemistry* 72(2):172-176 (1995).

Greenwell, P. and J.D. Schofield, "A Starch Granule Protein Associated with Endosperm Softness In Wheat," *Cereal Chemistry* 63(4):379-380 (1986).

Hill et al., "Functional Analysis of conserved histidines in ADP-Glucose pyrophosphorylase from *Escherichia coli*," *Biochemical and Biophysical Research Communications* 244:573-577 (1998) Article No. RC988301.

Ishida, Y., et al., "High Efficiency Transformation of Maize (*Zea mays* L.) Mediated by *Agrobacterium tumefaciens*," *Nature Biotecnology* 14:745-750 (1996).

Jolly, C.J., S. Rahman, A.A. Kortt, and T.J.V. Higgins, "Characterisation of the Wheat Mr 15000 "Grain Softness Protein" and Analysis of the Relationship Between its Accumulation in the Whole Seed and Grain Softness," *Theoretical and Applied Genetics* 86:589-597 (1993).

Krishnamurthy, K., and M.J. Giroux, "Expression of Wheat Puroindoline Genes in Transgenic Rice Enhances Grain Softness," *Nature Biotechnology* 19:162-166 (2001).

Krishnamurthy, "Wheat Puroindolines Enhance Fungal Disease Resistance in Transgenic Rice," 14(10):1255-1260 (2001), Mol. Plant Microbe Interact.

Lazar et al., "Transforming Growth Factor a: Mutation of Aspartic Acid 47 and Leucine 48 Results in Different Biological Activities," *Molecular and Cellular Biology* p. 1247-1252 (1998).

Morris, C.F., G.A. Greenblatt, A.D. Bettge and H.I. Malkawi, "Isolation and Characterization of Multiple Forms of Friabilin," *Journal of Cereal Science* 21: 167-174 (1994).

Morris, C.F. and S.P. Rose, "Wheat," In *Cereal Grain Quality*, R.J. Henry and P.S. Kettlewell (eds.), Chapman and Hall, New York, N.Y. p. 3-54 (1996).

Morris, C.F., Puroindolines: the molecular genetic basis of wheat grain hardness, *Plant Molecular Biology* 48:633-647 (2002).

TRANSGENIC PLANTS EXPRESSING PUROINDOLINES AND METHODS FOR PRODUCING SUCH PLANTS

CROSS REFERENCES TO RELATED APPLICATIONS

This application is a division of U.S. patent application Ser. No. 09/489,674, filed Jan. 24, 2000, now U.S. Pat. No. 6,600, 090, which is a continuation-in-part of U.S. patent application Ser. No. 09/083,852, filed on May 22, 1998, now U.S. Pat. No. 6,596,930 and is related to PCT/US99/11379, filed on May 21, 1999. All prior applications are hereby incorporated by reference in their entireties, including any associated sequence listings.

FIELD OF THE INVENTION

This invention relates to pest control in plants. More specifically, this invention relates to methods for producing transgenic plant cells, plant tissues and whole plants which express effective anti-pathogen proteins and the transgenic cells, tissues and plants produced by such methods. Even more specifically, this invention relates to methods for producing transgenic plant cells, plant tissues and whole plants which express puroindoline proteins and the transgenic cells, tissues and plants produced by such methods. This invention also relates to isolated nucleic acid molecules which include a promoter operably linked to nucleic acids coding for one or more puroindoline proteins.

BACKGROUND

All publications and patent applications herein are incorporated by reference to the same extent as if each individual publication or patent application was specifically and individually indicated to be incorporated by reference.

Higher plants primarily use three methods to limit or decrease the growth of pathogens: 1) the hypersensitive or gene-for-gene response; 2) inducible responses such as systemic acquired resistance; and 3) via antimicrobial peptides.

Anti-microbial peptides act as a type of innate immunity which limits pathogen growth and spread. This mechanism may play an important role in a plant's natural defenses against pathogens. Thionins, defensins, and non-specific lipid transfer proteins (nsLTPs) are the most common plant proteins reported to have anti-microbial properties (reviewed in Garcia-Olmedo et al., 1995; Broekaert et al., 1997).

Most experiments utilizing plants transgenic for anti-microbial peptides have assessed the effects of the over-expression of endogenous or heterologous anti-microbial proteins. For example, transgenic tobacco plants with constitutive expression of the barley LTP2 protein (Molina and Garcia-Olmedo, 1997) or the barley alpha-thionin (Carmona et al., 1993) showed much reduced bacterial pathogen infection on leaf tissue. Over-expression of endogenous thionin genes in *Arabidopsis thaliana* (Epple et al., 1997) also resulted in reduced wilt symptoms upon infection by *Fusarium oxysporum*. Molina et al. (1997, *Plant J.* 12(3):669-675) report the expression of the barley lipid transfer protein LTP2 in transgenic tobacco. Some of these genes have been demonstrated to be inducible by pathogen infection (Molina et al., 1996).

Synergistic enhancement of anti-microbial properties has been demonstrated in vitro for a number of different anti-microbial proteins (Dubreil et al., 1998; Terras et al., 1993). The effects of multiple anti-microbial proteins may be expected to be at least additive.

There is a continuing need for alternative and supplementary methods of protecting plants from plant pests, including plant pathogens.

This invention provides for the control of pests via introduction of the puroindoline a gene (pinA) and the puroindoline b gene (pinB) into plant cells, plant tissues and plants. The constitutive protection offered by the PINA and PINB proteins, either singly or together, is surprising since these proteins are not part of an inducible defense found naturally in plants. Assessment of the inhibitory effect of the PINA and PINB proteins on pathogen growth on leaf tissue as demonstrated in the present invention is also unexpected since pinA and pinB are not expressed at all in normal leaf tissue (i.e., no puroindoline gene homologues are expressed in leaf tissue.). Prior to the present invention, no demonstration of in vivo anti-microbial properties has been demonstrated for the puroindolines. Thus, the present invention provides a new and important set of tools and methods for the protection of plants to pests which affect plant growth and yield.

SUMMARY OF THE INVENTION

This invention provides plant cells, plant tissues and plants transgenic for nucleic acids encoding puroindolines.

This invention further provides plant cells, plant tissues and plants transgenic for nucleic acids which hybridize under high stringency conditions with nucleic acids encoding puroindolines.

This invention also provides plant cells, plant tissues and plants transgenic for nucleic acids encoding fragments of puroindolines wherein the fragments retain at least one biological activity of the puroindolines.

This invention further provides plant cells, plant tissues or plants transgenic for recombinant DNA sequences encoding either or both of puroindolineA and puroindolineB.

This invention also provides plants which are transgenic for any of the above-listed nucleic acids, wherein the transgenic plants are capable of exhibiting a reduction in plant damage of greater than about 5% when compared to the corresponding non-transgenic plants following exposure of the transgenic plants and the corresponding non-transgenic plants to pests capable of damaging the plants. More specifically, this invention provides such transgenic plants wherein the transgenic plants are capable of exhibiting a reduction in plant damage of between about 5% and about 10%, or of between about 10% and about 20%, or of between about 20% and about 30%, or of between about 30% and about 40%, or of between about 40% and about 50%, or of between about 50% and about 60%, or of between about 60% and about 70%, or of between about 70% and about 80%, or of between about 80% and about 90%, or of between about 90% and about 100%, when compared to the corresponding non-transgenic plants following exposure of the transgenic plants and the corresponding non-transgenic plants to pests capable of damaging the plants. The pests which may be effectively controlled using the transgenic plants of the present invention include, but are not limited to, fungi, bacteria, viruses, nematodes, insects and mites. Of the insect and mite pests, the ones that are of particular importance to the present invention, include, but are not limited to, thoses that carry plant pathogens.

This invention provides monocotyledonous and dicotyledonous plants comprising either or both of puroindolineA and puroindolineB present in leaf tissue in an amount effective to reduce disease symptoms in response to infection by a pathogen. Such plants include, but are not limited to, maize, rice, wheat, barley, rye, canola, potatoes, tomatoes, sweet potatoes, sugar beets, tobacco, and cotton. More specifically this invention provides such plants wherein the pathogen is a fungus.

This invention further provides isolated nucleic acid molecules comprising nucleic acids operatively linked to constitutive or inducible promoters in a manner effective for expression of the nucleic acids, wherein the nucleic acids are selected from the group consisting of nucleic acids encoding one or more puroindolines, nucleic acids which hybridizes under high stringency conditions to the nucleic acids encoding puroindolines, and nucleic acids encoding fragments of a puroindoline wherein the fragments retain at least one biological activity of a puroindoline. This invention also provides methods of producing transformed plant cells, plant tissues or plants by transforming the plant cells, plant tissues or plants with such isolated nucleic acid molecules. This invention further provides methods of crossing the transformed plants to different plants, harvesting the resultant seeds, and planting and growing the harvested seeds.

DETAILED DESCRIPTION OF THE INVENTION

I. Definitions.

As used herein, the term "allele" means any of several alternative forms of a gene.

As used herein, the term "crop plant" means any plant grown for any commercial purpose, including, but not limited to the following purposes: seed production, hay production, ornamental use, fruit production, berry production, vegetable production, oil production, protein production, forage production, silage, animal grazing, golf courses, lawns, flower production, landscaping, erosion control, green manure, improving soil tilth/health, producing pharmaceutical products/drugs, producing food additives, smoking products, pulp production and wood production. Particular crop plants of interest to the present invention include, but are not limited to, wheat, rice, maize, barley, rye, sugar beets, potatoes, sweet potatoes, soybeans, cotton, tomatoes, canola and tobacco.

As used herein, the term "cross pollination" or "crossbreeding" means the pollen of one flower on one plant is applied (artificially or naturally) to the ovule (stigma) of a flower on another plant.

As used herein, the term "cultivar" means a variety, strain or race of plant which has been produced by horticultural or agronomic techniques and is not normally found in wild populations.

As used herein, the term "damage" is synonymous with "plant damage" and means any injury to a plant caused by any pest. Examples of plant damage include, but are not limited to, reduced shoot growth, reduced root growth, root pruning, necrotic leaf spots, lodging, wilting, stunting, chlorosis, broken tops, reduced branching, reduced flowering, flower abortion, ovule abortion, pollen abortion, yellowing of the leaf, lesions, internal stem discoloration, decayed roots, discolored stems, stalk tunneling, insect feeding, defoliation, reduced vigor, reduction in seed quality or viability and dead and dying plants.

As used herein, the terms "Dicotyledoneae", "dicotyledonous", "dicotyledon" or "dicot" are synonymous and mean any of various flowering plants having two embryonic seed leaves or cotyledons that usually appear at germination. Examples include, but are not limited to, tobacco, soybeans, potato, sweet potato, radish, cabbage, rape and apple trees.

As used herein, the term "disease" is synonymous with "plant disease" and means an infection by a pathogen.

As used herein, the term "genotype" means the genetic makeup of an individual cell, cell culture, plant, or group of plants.

As used herein, the term "heterozygote" means a diploid or polyploid individual cell or plant having different alleles (forms of a given gene) at least at one locus.

As used herein, the term "heterozygous" means the presence of different alleles (forms of a given gene) at a particular gene locus.

As used herein, the term "homozygote" means an individual cell or plant having the same alleles at one or more loci.

As used herein, the term "homozygous" means the presence of identical alleles at one or more loci in homologous chromosomal segments.

As used herein, the term "hybrid" means any individual plant resulting from a cross between parents that differ in one or more genes.

As used herein, the term "inbred" or "inbred line" means a relatively true-breeding strain.

As used herein, a nucleic acid molecule is said to be "isolated" when the nucleic acid molecule is substantially separated from contaminant nucleic acid encoding other polypeptides from the source of nucleic acid.

As used herein, the term "line", when directed to a type of plant, means self- or cross-fertilizing plants and single-line facultative apomicts, having largely the same genetic background, that are similar in essential and distinctive characteristics.

As used herein, the term "locus" (plural: "loci") means any site that has been defined genetically. A locus may be a gene, or part of a gene, or a DNA sequence that has some regulatory role, and may be occupied by different sequences.

As used herein, the term "mass selection" means a form of selection in which individual plants are selected and the next generation propagated from the aggregate of their seeds.

As used herein, the terms "Monocotyledoneae", "monocotyledonous", "monocotyledon" or "monocot" are synonymous and mean any of various flowering plants having a single cotyledon in the seed. Examples of monocots include, but are not limited to, rice, wheat, barley, maize and lilies.

As used herein, the term "Northern Blot" refers to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (Sambrook et al., *Molecular Cloning: A Laboratory Manual,* 2nd edition, Cold Spring Harbor Laboratory Press, 1985).

As used herein, the term "open pollination" means a plant population that is freely exposed to some gene flow, as opposed to a closed one in which there is an effective barrier to gene flow.

As used herein, the terms "open-pollinated population" or "open-pollinated variety" mean plants normally capable of at least some cross-fertilization, selected to a standard, that may show variation but that also have one or more genotypic or phenotypic characteristics by which the population or the variety can be differentiated from others. A hybrid which has no barriers to cross-pollination is an open-pollinated population or an open-pollinated variety.

As used herein, the term "ovule" means the female gametophyte, whereas the term "pollen" means the male gametophyte.

As used herein, the term "pathogen" means a disease-producing agent, especially a microorganism. Examples of pathogens include, but are not limited to, bacteria, fungi, viruses and nematodes.

As used herein, the term "pest" means a pathogen, insect, or arachnid that damages or injures a plant. Thus, the term "pest" as used herein includes, but is not limited to, bacteria, fungi, viruses, nematodes, insects and mites. Insects (e.g., thrips) and mites (e.g., spider mites) which transmit plant pathogens are particular animal targets of the present invention. Specific examples of pests include, but are not limited to, alfalfa mosaic virus, wheat streak mosaic virus, bacterial blights, thrips, boll weevils, soybean cyst nematode, spider mites, Hessian fly, army cutworm, brown wheat mite, ants, corn borers and gypsy moths.

As used herein, the term "phenotype" means the observable characters of an individual cell, cell culture, plant, or group of plants which results from the interaction between that individual's genetic makeup (i.e., genotype) and the environment.

As used herein, the term "progeny" means the descendants of a particular plant (self-cross) or pair of plants (crossed or backcrossed). The descendants can be of the $F_1$, the $F_2$, or any subsequent generation. Typically, the parents are the pollen donor and the ovule donor which are crossed to make the progeny plant of this invention. Parents also refer to $F_1$ parents of a hybrid plants of this invention (the $F_2$ plants). Finally, parents refer to a recurrent parent which is backcrossed to hybrid plants of this invention to produce another hybrid plant of this invention.

As used herein, the term "Polymerase Chain Reaction" is synonymous with "PCR" and refers to techniques in which cycles of denaturation, annealing with primer, and extension with DNA polymerase, are used to amplify the number of copies of a target DNA sequence.

As used herein, the term "resistance" means a host plant's more or less total capacity to fight a pest, wherein the resistance is usually due to a gene-for-gene resistance.

As used herein, the term "rice" means any *Oryza* species, including, but not limited to, *O. sativa, O. glaberrima, O. perennis, O. nivara*, and *O. breviligulata*. Thus, as used herein, the term "rice" means any type of rice including, but is not limited to, any cultivated rice, any wild rice, any rice species, any intra- and inter-species rice crosses, all rice varieties, all rice genotypes and all rice cultivars.

As used herein, the term "self pollinated" or "self-pollination" means the pollen of one flower on one plant is applied (artificially or naturally) to the ovule (stigma) of the same or a different flower on the same plant.

As used herein, the term "synthetic" means a set of progenies derived by intercrossing a specific set of clones or seed-propagated lines. A synthetic may contain mixtures of seed resulting from cross-, self-, and sib-fertilization.

As used herein, the term "tolerance" means a host plant's partial capacity to fight a pest, wherein the tolerance is not necessarily due to a gene-for-gene resistance.

As used herein, the term "tomato" means any *Lycopersicon* species, including, but not limited to, *L. cheesmanii* Riley, *L. chilense* Dun., *L. esculentum f. pyrforme* (Dun.) C. H. Muller, *L. esculenturn* Mill., *L. esculmentum* var. *cerasforme* (Dun.) A. Gray, *L. hirsutum* Humb. & Bonpl., *L. peruvianum* (L.) Mill., and *L. pimpinellfolium* (L.) Mill. Thus, as used herein, the term "tomato" means any type of tomato including, but is not limited to, any cultivated tomato, any wild tomato, any tomato species, any intra- and inter-species tomato crosses, all tomato varieties, all tomato genotypes and all tomato cultivars. Cultivated tomatoes include, but are not limited to, pear tomatoes, Italian tomatoes, cherry tomatoes, canning tomatoes, sauce tomatoes and beef tomatoes.

As used herein, the term "transformation" means the transfer of nucleic acid (i.e., a nucleotide polymer) into a cell. As used herein, the term "genetic transformation" means the transfer and incorporation of DNA, especially recombinant DNA, into a cell.

As used herein, the term "transgenic" means cells, cell cultures, plants, and progeny of plants which have received a foreign or modified gene by one of the various methods of transformation, wherein the foreign or modified gene is from the same or different species than the species of the plant receiving the foreign or modified gene. As used herein, the terms "transgenic plant" and "transformed plant" are synonymous, as are the terms "transgenic line" and "transformed line". As used herein, the phrases "corresponding non-transgenic plant" and "corresponding non-transgenic line" refer to the cells, cell cultures, plants and progeny of plants which did not receive the foreign or modified gene which the "transgenic" cells, cell cultures, plants and progeny of plants which did receive the foreign or modified gene.

As used herein, the term "variety" means a subdivision of a species, consisting of a group of individuals within the species which are distinct in form or function from other similar arrays of individuals.

As used herein, the term "wheat" means any *Triticum* species, including, but not limited to, *T. aestivum, T. monococcum, T. tauschii* and *T. turgidum*. Thus, as used herein, the term "wheat" means any type of wheat including, but is not limited to, any cultivated wheat, any wild wheat, any wheat species, any intra- and inter-species wheat crosses, all wheat varieties, all wheat genotypes and all wheat cultivars. Cultivated wheats include, but are not limited to, einkorn, durum and common wheats.

II. Nucleic Acids Encoding Puroindolines.

Gautier et al. (1994, *Plant Mol. Bio.* 25:43-57) isolated and sequenced cDNA clones encoding the two puroindolines from a mid-maturation seed cDNA library (see FIGS. 1, 2 and 3 of the article) (see also, GenBank Accession Numbers X69912 (SEQ ID NO. 5), X69913 (SEO ID NO. 7) and X69914 (SEQ ID NO. 9) for the nucleotide sequences; GenBank Accession Numbers S46514 (SEQ ID NO. 6), S46515 (SEQ ID NO. 8), CAA49538 (SEQ ID NO. 8), and CAA49539 (SEQ ID NO. 10) for the amino acid sequences). The Gautier et al. article and the associated sequences, including FIGS. 1, 2 and 3 of the article and the associated GenBank accessions, arc specifically incorporated by reference herein in their entirety.

As used herein, puroindoline genes include the specifically identified and characterized variants herein described as well as allelic variants, conservative substitution variants and homologues that can be isolated/generated and characterized without undue experimentation following methods well known to one skilled in the art.

Homology or identity at the amino acid or nucleotide level is determined by BLAST (Basic Local Alignment Search Tool) analysis using the algorithm employed by the programs blastp, blastn, blastx, tblastn and tblastx (Karlin et al., 1990, *Proc. Natl. Acad. Sci. USA* 87, 2264-2268 and Altschul, 1993, *J. Mol. Evol.*36, 290-300, fully incorporated by reference) which are tailored for sequence similarity searching. The approach used by the BLAST program is to first consider similar segments between a query sequence and a database sequence, then to evaluate the statistical significance of all matches that are identified and finally to summarize only those matches which satisfy a preselected threshold of significance. For a discussion of basic issues in similarity searching of sequence databases (see Altschul et al., 1994, *Nature Genetics* 6, 119-129 which is fully incorporated by reference). The search parameters for histogram, descriptions, alignments, expect (i.e., the statistical significance threshold for reporting matches against database sequences), cutoff, matrix and filter are at the default settings. The default scoring matrix used by blastp, blastx, tblastn, and tblastx is the BLOSUM62 matrix (Henikoff et al., 1992, *Proc. Natl. Acad. Sci. USA* 89, 10915-10919, fully incorporated by reference). For blastn, the scoring matrix is set by the ratios of M (i.e., the reward score for a pair of matching residues) to N (i.e., the penalty score for mismatching residues), wherein the default values for M and N are 5 and −4, respectively.

The terms "puroindoline genes", "pinA genes", or "pinB genes" include all naturally occurring allelic variants of the puroindoline genes exemplified herein.

The puroindoline nucleic acid molecules or fragment thereof utilized in the present invention may also be synthesized using methods known in the art. It is also possible to produce the molecule by genetic engineering techniques, by constructing DNA using any accepted technique, cloning the DNA in an expression vehicle and transfecting the vehicle into a cell which will express the puroindoline proteins. See, for example, the methods set forth in Sambrook et al., *Molecular Cloning: A Laboratory Manual*, 2nd edition, Cold Spring Harbor Laboratory Press, 1985.

The phrase "puroindoline protein" refers to a class of proteins, including but not limited to, "puroindoline A" or "puro A" and "puroindoline B" or "puro B". Puro A and puro B have tryptophan-rich hydrophobic domains which have affinity for binding lipids, referred to herein as "the lipid-binding domains" (Blocket et al., 1991, *Gluten Proteins* 1990, Bushak & Tkachuk (eds.), American Association of Cereal Chemists, St. Paul, Minn.; Wilde et al., 1993, *Agric. Res.* 20:971)). It is understood that all polynucleotides encoding all or a portion of the puroindoline proteins used in the present invention are also included herein, as long as they encode a polypeptide with one or more of the functional activities of the puroindoline proteins as set forth herein. Thus, any polynucleotide fragment having the activities of the puroindolines discussed herein are encompassed by the present invention.

Polynucleotide sequences of the invention include DNA, cDNA, synthetic DNA and RNA sequences which encode puroindoline proteins. Such polynucleotides also include naturally occurring, synthetic and intentionally manipulated polynucleotides. For example, such polynucleotide sequences may comprise genomic DNA which may or may not include naturally occurring introns. Moreover, such genomic DNA may be obtained in association with promoter regions or poly A sequences. As another example, portions of the mRNA sequence may be altered due to alternate RNA splicing patterns or the use of alternate promoters for RNA transcription. As yet another example, puroindoline polynucleotides may be subjected to site-directed mutagenesis.

The polynucleotides of the invention further include sequences that are degenerate as a result of the genetic code. The genetic code is said to be degenerate because more than one nucleotide triplet codes for the same amino acid. There are 20 natural amino acids, most of which are specified by more than one codon. It will be appreciated by those skilled in the art that as a result of the degeneracy of the genetic code, a multitude of nucleotide sequences, some bearing minimal nucleotide sequence homology to the nucleotide sequence of pinA and pinB may be utilized in the present invention. Therefore, all degenerate nucleotide sequences are included in the invention as long as the amino acid sequence of the puroindoline polypeptides encoded by the nucleotide sequence are functionally unchanged or substantially similar in function. The invention specifically contemplated each and every possible variation of peptide or nucleotide sequence that could be made by selecting combinations based on the possible amino acid and codon choices made in accordance with the standard triplet genetic code as applied to the puroindoline sequences of the invention, as exemplified by pinA and pinB, and all such variations are to be considered specifically disclosed herein.

Also included in the invention are fragments (portions, segments) of the sequences disclosed herein which selectively hybridize to pinA and pinB. Selective hybridization as used herein refers to hybridization under stringent conditions (See, for example, the techniques in Maniatis et al., *Molecular Cloning: A Laboratory Manual*, Cold Spring Harbor Laboratory Press, 1989), which distinguishes related from unrelated nucleotide sequences. The active fragments of the invention, which are complementary to mRNA and the coding strand of DNA, are usually at least about 15 nucleotides, more usually at least 20 nucleotides, preferably 30 nucleotides and more preferably may be 50 nucleotides or more.

"Stringent conditions" are those that (1) employ low ionic strength and high temperature for washing, for example, 0.5 M sodium phosphate buffer pH 7.2, 1 mM EDTA pH 8.0 in 7% SDS at either 65° C. or 55° C., or (2) employ during hybridization a denaturing agent such as formamide, for example, 50% (vol/vol) formamide with 0.1% bovine serum albumin, 0.1% Ficoll, 0.1% polyvinylpyrrolidone, 0.05 M sodium phosphate buffer at pH 6.5 with 0.75 M NaCl, 0.075 M sodium citrate at 42° C. Another example is use of 50% formamide, 5×SSC (0.75 M NaCl, 0.075 M sodium citrate), 50 mM sodium phosphate (pH 6.8), 0.1% sodium pyrophosphate, 5× Denhardt's solution, sonicated salmon sperm DNA (50 μg/ml), 0.1% SDS, and 10% dextran sulfate at 55° C., with washes at 55° C. in 0.2×SSC and 0.1% SDS. A skilled artisan can readily determine and vary the stringency conditions appropriately to obtain a clear and detectable hybridization signal. Preferred molecules are those that hybridize under the above conditions to the complements of pinA and pinB and which encode a functional protein.

The present invention utilizes nucleic acid molecules encoding puroindoline proteins which hybridize with nucleic acid molecules comprising sequences complimentary to pinA and pinB under conditions of sufficient stringency to produce a clear signal. As used herein, "nucleic acid" is defined as RNA or DNA encoding puroindoline peptides, or are complimentary to nucleic acids encoding such peptides, or hybridize to such nucleic acids and remain stably bound to them under stringent conditions, or encode polypeptides sharing at least 60% sequence identity, or at least 65% sequence identity, or at least 70% sequence identity, or at least 75% sequence identity, or at least 80% sequence identity, or at least 85% sequence identity, preferably at least 90% sequence identity, and more preferably at least 95% sequence identity with the PINA and PINB peptide sequences.

Plants naturally contain wildtype pinA and pinB genes that code for wildtype PINA and PINB, respectively. Wildtype, when referring to nucleic acid sequences or protein sequences, means the genetic constitution of an organism in which a number of mutations (markers) may already exist at the start of a program of mutagenesis before further changes are introduced. Thus, the wildtype PINA and PINB proteins refers to the various forms of the puroindoline proteins found naturally before the introduction of a nucleotide sequence coding for the wildtype pinA and pinB genes.

The present invention further provides fragments of any one of the encoding nucleic acids molecules. As used herein, a fragment of an encoding nucleic acid molecule refers to a small portion of the entire protein coding sequence. The size of the fragment will be determined by the intended use. For example, if the fragment is chosen so as to encode an active portion of the protein, the fragment will need to be large enough to encode the functional region(s) of the protein. For instance, fragments of the invention encode the lipid binding domains or regions of the puroindolines of the present invention. If the fragment is to be used as a nucleic acid probe or PCR primer, then the fragment length is chosen so as to obtain a relatively small number of false positives during probing and priming.

Fragments of the encoding nucleic acid molecules of the present invention (i.e., synthetic oligonucleotides) that are used as probes or specific primers for the polymerase chain reaction (PCR), or to synthesize gene sequences encoding proteins of the invention can easily be synthesized by chemical techniques, for example, the phosphotriester method of Matteucci et al., (1981) J. Am. Chem. Soc. 103, 3185-3191) or using automated synthesis methods. In addition, larger DNA segments can readily be prepared by well known methods, such as synthesis of a group of oligonucleotides that define various modular segments of the gene, followed by ligation of oligonucleotides to build the complete modified gene.

The encoding nucleic acid molecules of the present invention may further be modified so as to contain a detectable label for diagnostic and probe purposes. A variety of such labels are known in the art and can readily be employed with the encoding molecules herein described. Suitable labels include, but are not limited to, biotin, radiolabeled nucleotides and the like. A skilled artisan can employ any of the art known labels to obtain a labeled encoding nucleic acid molecule.

Modifications to the primary structure itself by deletion, addition, or alteration of the amino acids incorporated into the protein sequence during translation can be made without destroying the activity of the protein. Such substitutions or other alterations result in proteins having an amino acid sequence encoded by a nucleic acid falling within the contemplated scope of the present invention.

III. Isolation of other Related Nucleic Acid Molecules

As described herein, the identification and characterization of the nucleic acid molecules encoding a puroindoline or a fragment of a puroindoline allows a skilled artisan to isolate nucleic acid molecules that encode other members of the protein family in addition to the sequences herein described. Further, the presently disclosed nucleic acid molecules allow a skilled artisan to isolate nucleic acid molecules that encode other members of the family of proteins in addition to the puroindolines disclosed herein.

Essentially, a skilled artisan can readily use any one of the amino acid sequences disclosed herein to generate antibody probes to screen expression libraries prepared from appropriate cells. Typically, polyclonal antiserum from mammals such as rabbits immunized with the purified protein or monoclonal antibodies can be used to probe a cDNA or genomic expression library to obtain the appropriate coding sequence for other members of the protein family. The cloned cDNA sequence can be expressed as a fusion protein, expressed directly using its own control sequences, or expressed by constructions using control sequences appropriate to the particular host used for expression of the enzyme.

Alternatively, a portion of the coding sequence herein described can be synthesized and used as a probe to retrieve DNA encoding a member of the protein family from any organism. Oligomers containing approximately 18-20 nucleotides (encoding about a six to seven amino acid stretch) are prepared and used to screen genomic DNA or cDNA libraries to obtain hybridization under stringent conditions or conditions of sufficient stringency to eliminate an undue level of false positives.

Additionally, pairs of oligonucleotide primers can be prepared for use in a polymerase chain reaction (PCR) to selectively clone an encoding nucleic acid molecule. A PCR denature/anneal/extend cycle for using such PCR primers is well known in the art and can readily be adapted for use in isolating other encoding nucleic acid molecules.

IV. Production of Recombinant Proteins using a rDNA Molecule

The present invention further provides methods for producing a puroindoline protein of the invention using the nucleic acid molecules herein described. In general terms, the production of a recombinant form of a protein typically involves the following steps: First, a nucleic acid molecule is obtained that encodes a puroindoline protein or a fragment of a puroindoline protein. If the encoding sequence is uninterrupted by introns, it is directly suitable for expression in any host. The nucleic acid molecule is then preferably placed in operable linkage with suitable control sequences, as described above, to form an expression unit containing the protein open reading frame. The expression unit is used to transform a suitable host and the transformed host is cultured under conditions that allow the production of the recombinant protein. Optionally the recombinant protein is isolated from the medium or from the cells; recovery and purification of the protein may not be necessary in some instances where some impurities may be tolerated.

Each of the foregoing steps can be done in a variety of ways. For example, the desired coding sequences may be obtained from genomic fragments and used directly in appropriate hosts. The construction of expression vectors that are operable in a variety of hosts is accomplished using appropriate replicons and control sequences, as set forth above. The control sequences, expression vectors, and transformation methods are dependent on the type of host cell used to express the gene and were discussed in detail earlier. Suitable restriction sites can, if not normally available, be added to the ends of the coding sequence so as to provide an excisable gene to insert into these vectors. A skilled artisan can readily adapt any host-expression system known in the art for use with the nucleic acid molecules of the invention to produce recombinant protein.

V. Puroindoline Proteins.

The puroindoline proteins PINA and PINB are wheat endosperm proteins believed to be involved in determining whether wheat grain is soft or hard textured (see, e.g., Rahman et al., 1994, *Eur. J. Biochem.* 223(3):917-925)(GenBank Accession Numbers S48186, S48187, S48188, CAA56595, CAA56596, CAA56597, CAA56598, AAC60577).

The amino acid sequences for puroindolineA and puroindolineB isolated from wheat (*Triticum aestivum*) endosperm were determined by Blochet et al. (1993, *FEBS* 329(3):336-340) (see FIG. 2 of the article)(see also, GenBank Accession Numbers AAB28037 and S36107). The Blochet et al. article and the associated sequences, including FIG. 2 of the article and the GenBank accessions, are specifically incorporated by reference herein in their entirety.

Blochet et al. (1993, supra) speculate on the possible antibacterial and antifungal properties of the puroindolines and the anti-fungal activity of the proteins has been observed in vitro, as noted by Dubreil et al. (*Plant Sci.,* 1998, 138:121-135). However, Gautier et al. (1994, supra) have noted that there is no experimental evidence available to support this assumed function of the puroindolines in seeds. In addition, Tanchak et al. (1998, Plant Sci. 137:173-184) stated the following:

Because of their tryptophan-rich domain which shows some similarity to the mammalian peptide, indolicidin, it has been speculated that puroindolines may be membrane-active toxins with antimicrobial activity. In actual fact, the noted similarity between indolicidin and the plant proteins, puroindolines, GSP and oat tryptophanins, is not particularly strong." (page 182, paragraph bridging columns 1-2)(citations and references omitted).

PinA and pinB are expressed only in wheat endosperm tissue (Gautier et al., 1994). Neither of these proteins is found in leaf tissue of any plants, nor are there apparent homologs of these genes in plant species outside the grass family.

As used herein, a puroindoline protein refers to a protein that has the amino acid sequence encoded by the polynucleotide of PINA and PINB, allelic variants thereof and conservative substitutions thereof that have puroindoline activity. In addition, the polypeptides utilized in the present invention include the proteins encoded by PINA and PINB, as well as polypeptides and fragments, particularly those which have the biological activity of PINA and PINB and also those which have at least 65% sequence identity to the polypeptides encoded by PINA and PINB or the relevant portion, or at least 70% identity, or at least 75% identity, or at least 80% identity, or at least 85% identity to the polypeptides encoded by PINA and PINB or the relevant portion, and more preferably at least 90% similarity to the polypeptides encoded by PINA and PINB or the relevant portion, and still more preferably at least 95% similarity to the polypeptides encoded by PINA and PINB or the relevant portion, and also include portions of such polypeptides. One of skill will recognize whether an amino acid sequence of interest is within a functional domain of a protein, such as the lipid-binding domain of the puroindolines used in the present invention. Thus, it may be possible for a homologous protein to have less than 40% homology over the length of the amino acid sequence but greater than 90% homology in one functional domain.

The puroindoline proteins utilized in the present invention include the specifically identified and characterized variants herein described as well as allelic variants, conservative substitution variants and homologues that can be isolated/generated and characterized without undue experimentation following the methods well known to one skilled in the art.

The term "substantially pure" as used herein refers to puroindoline polypeptides which are substantially free of other proteins, lipids, carbohydrates or other materials with which they are naturally associated. One skilled in the art can purify puroindolines using standard techniques for protein purification.

The invention also utilizes amino acid sequences coding for isolated puroindoline polypeptides. The polypeptides of the invention include those which differ from the exemplified puroindoline proteins as a result of conservative variations. The terms "conservative variation" or "conservative substitution" as used herein denotes the replacement of an amino acid residue by another, biologically similar residue. Conservative variations or substitutions are not likely to change the shape of the polypeptide chain. Examples of conservative variations, or substitutions, include the replacement of one hydrophobic residue such as isoleucine, valine, leucine or methionine for another, or the substitution of one polar residue for another, such as the substitution of arginine for lysine, glutamic for aspartic acid, or glutamine for asparagine, and the like. Therefore, all conservative substitutions are included in the invention as long as the puroindoline polypeptides encoded by the nucleotide sequence are functionally unchanged or similar.

As used herein, an isolated puroindoline protein can be a full-length PINA or PINB or any homologue of such proteins, such as puroindoline proteins in which amino acids have been deleted (e.g., a truncated version of the protein, such as a peptide), inserted, inverted, substituted and/or derivatized (e.g., by glycosylation, phosphorylation, acetylation, myristoylation, prenylation, palmitoylation, amidation and/or addition of glycosylphosphatidyl inositol), wherein modified protein retains the physiological characteristics of natural puroindoline proteins. A homologue of a puroindoline protein is a protein having an amino acid sequence that is sufficiently similar to a natural puroindoline protein amino acid sequence that a nucleic acid sequence encoding the homologue is capable of hybridizing under stringent conditions to (i.e., with) a nucleic acid sequence encoding the natural puroindoline protein amino acid sequence. Appropriate stringency requirements are discussed above.

Puroindoline protein homologues can be the result of allelic variation of a natural gene encoding a puroindoline protein. Natural genes are also referred to as "wildtype genes." A natural, or wildtype, gene refers to the form of the gene found most often in nature. Puroindoline protein homologues can be produced using techniques known in the art including, but not limited to, direct modifications to a gene encoding a protein using, for example, classic or recombinant DNA techniques to effect random or targeted mutagenesis.

Minor modifications of the PINA and PINB primary amino acid sequence may result in proteins which have substantially equivalent activity as compared to the puroindolines produced by the genes described herein. As used herein, a "functional equivalent" of a puroindoline protein is a protein which possesses a biological activity or immunological characteristic substantially similar to a biological activity or immunological characteristic of non-recombinant, or natural, puroindoline. The term "functional equivalent" is intended to include the fragments, variants, analogues, homologues, or chemical derivatives of a molecule which possess the biological activity of the puroindoline proteins encoded by the genes of the present invention.

The terms "puroindoline proteins", "PINA proteins" and "PINB proteins" include all naturally occurring allelic variants of these proteins that possess normal puroindoline activity. In general, allelic variants of PINA and PINB proteins will have slightly different amino acid sequence than that specifically encoded by the genes utilized in the present invention but will be able to produce the exemplified phenotypes. Allelic variants, though possessing a slightly different amino acid sequence than those recited above, will posses the ability to produce a phenotype which exhibits the ability to retard, limit or prevent pathogen infection, growth and/or reproduction.

The methods of the present invention can be used by one skilled in the art of plant breeding and plant husbandry to produce crop plants with improved characteristics for pathogen tolerance or resistance.

Applicants further teach methods of recognizing variations in the DNA sequences of pinA and pinB. One method involves the introduction of a nucleic acid molecule (also known as a probe) having a sequence complementary to the puroindoline genes utilized in the invention under sufficient hybridizing conditions, as would be understood by those in the art. Another method of recognizing DNA sequence variation associated with pinA and pinB is direct DNA sequence analysis by multiple methods well known in the art. Another embodiment involves the detection of DNA sequence variation in the puroindolines as represented by different plant genera, species, strains, varieties or cultivars. PinA and pinB can be used as probes to detect the presence of puroindoline genes in other plants. As discussed previously, pinA and pinB sequences have been determined and are readily available to one of ordinary skill in the art. In one embodiment, the sequences will bind specifically to one allele of a puroindoline gene, or a fragment thereof, and in another embodiment will bind to multiple alleles. Such detection methods include the polymerase chain reaction, restriction fragment length polymorphism (RFLP) analysis and single stranded conformational analysis.

Diagnostic probes useful in such assays of the invention include antibodies to PINA and PINB. The antibodies may be either monoclonal or polyclonal, produced using standard techniques well known in the art (See Harlow & Lane's *Antibodies: A Laboratory Manual*, Cold Spring Harbor Laboratory Press, 1988). They can be used to detect puroindoline proteins by binding to the protein and subsequent detection of the antibody-protein complex by ELISA, Western blot or the like. Antibodies are also produced from peptide sequences of PINA and PINB using standard techniques in the art (See *Protocols in Immunology*, John Wiley & Sons, 1994). Fragments of the monoclonals or the polyclonal antisera which contain the immunologically significant portion can also be prepared.

Assays to detect or measure puroindoline polypeptides in a biological sample with an antibody probe may be based on any available format. For instance, in immunoassays where puroindoline polypeptides are the analyte, the test sample, typically a biological sample, is incubated with anti-pinA or pinB antibodies under conditions that allow the formation of antigen-antibody complexes. Various formats can be employed, such as "sandwich" assay where antibody bound to a solid support is incubated with the test sample; washed, incubated with a second, labeled antibody to the analyte; and the support is washed again. Analyte is detected by determining if the second antibody is bound to the support. In a competitive format, which can be either heterogeneous or homogeneous, a test sample is usually incubated with an antibody and a labeled competing antigen, either sequentially or simultaneously. These and other formats are well known in the art.

VI. Plant Pathogens.

As discussed above, the term "pathogen" means a disease-producing agent, especially a microorganism. Examples of pathogens include, but are not limited to, bacteria, fungi, viruses and nematodes.

Rice Blast. Blast, caused by *Magnaporthe grisea*, is considered to be the major fungal disease of rice. Blast infection of leaves can cause damage to the crop by reducing the green leaf area and in severe cases an entire planting can be destroyed. Panicle blast occurs in nearly all mature plants and infection directly causes severe yield losses or total crop failure. Because of the instability of the blast fungus and the marked variability in pathogenicity found in different strains of the organism, control through breeding has only met with partial success.

The fungus *M. grisea* shows high variability with respect to host range and cultivar specificity. About 50 gramineous hosts and some other non-grass hosts been reported to be parasitized by this fungus (Asuyama, 1965; Ou, 1985).

Sheath Blight of Rice. Sheath blight (ShB) of rice caused by *Rhizoctonia solani*, is an economically important disease of rice, being second only to rice blast among the fungal diseases.

ShB occurs throughout the rice production areas of the world, in both the tropical and temperate climates. ShB disease yield losses can reach 50% with susceptible cultivars when a severe infection is well distributed in the field. Countries like Japan, Vietnam, Korea and Southern US have reported severe crop losses due to ShB. Attempts to control ShB using resistant cultivars have not been successful because of low levels of available host resistance.

*R. solani* infects a wide range of plants of 188 species in 32 families (Kozaka, 1965). When eighteen species and 817 cultivars of rice were tested; none of them were physiologically resistant to *R. solani* (Hori, unpublished). ShB pathogen also infects 20 species of weeds that belong to 11 families of Gramineae and Cyperaceae (Tsai, 1970). In rice, greatest loss in yield due to ShB results when initial plant infection occurs during the late vegetative and early reproductive growth stage (Lee and Rush, 1983).

Common Bunt of Wheat. Bunt is one of four distinctly different smut diseases of wheat. Bunt is further separated into common and dwarf bunt, which are caused by different pathogen species and differ in symptoms, disease cycle and environmental requirements. Common bunt is caused by two related fungal species, inciting the same disease.

The bunts are characterized by the replacement of the normal kernel by a sorus, called a bunt ball, composed of fungal spores enclosed in the host pericarp. For a more detailed description of common bunt, see J. S. Schafer, 1987, Rusts, Smuts and Powdery Mildew. In Wheat and Wheat Improvement, Second Edition, E. G. Heyne, ed., Ch. 8C:542-584, American Society of Agronomy.

Historically, bunt has been the most destructive of the wheat smuts in the United States. While hexachlorobenzene seed treatment has reduced the incidence and severity of the disease in the agriculturally developed areas of the world, serious losses continue in less-developed regions. Common bunt not only reduces yield, but the contamination of the grain by the spores also reduces quality for milling or feed.

Dwarf Bunt. Symptoms are similar to those of common bunt except for the additional characteristic of extreme dwarfing of infected plants.

Karnal Bunt. In contrast to common bunt, this disease is characterized by a partial infection of plants and kernels. The sorus containing the fungal spores replaces a variable portion of the kernel, usually along the longitudinal furrow and into the endosperm and scutulum.

Bacterial Spot Disease. *Xanthomonas campestris* cv. *vesicatoria* is the causal agent of bacterial spot disease on pepper and tomato plants.

Tomato Leaf Mold. *Cladosporium fulvum* (Cooke) (syn. *Fulvia fulva* [Cooke] Cif) is the causal agent of tomato leaf mold disease.

VII. Transformation Methods.

Methods of producing transgenic plants are well known to those of ordinary skill in the art. Transgenic plants can now be produced by a variety of different transformation methods including, but not limited to, electroporation; microinjection; microprojectile bombardment, also known as particle acceleration or biolistic bombardment; viral-mediated transformation; and Agrobacterium-mediated transformation (see, e.g., U.S. Pat. Nos. 5,405,765, 5,472,869, 5,538,877, 5,538,880, 5,550,318, 5,641,664, 5,736,369 and 5,736,369; Watson et al., *Recombinant DNA*, Scientific American Books (1992); Hinchee et al., *Bio/Tech.* 6:915-922 (1988); McCabe et al., *Bio/Tech.* 6:923-926 (1988); Toriyama et al., *Bio/Tech.* 6:1072-1074 (1988); Fromm et al., *Bio/Tech.* 8:833-839 (1990); Mullins et al., *Bio/Tech.* 8:833-839 (1990); and, Raineri et al., *Bio/Tech.* 8:33-38 (1990)).

Many of the manipulations being carried out in crop plants are meant for disease and pest resistance, product quality and tolerance to environmental stresses. Dale et al. (1993) reported that there were 395 transgenic plants approved for yield releases in different countries up to 1991. Logemann et al. (1992) have reported the expression of a barley ribosome-inactivating protein which afforded increased protection against *R. solani* in transgenic tobacco. Song et al. (1995) reported the expression of a receptor kinase-like protein which was encoded by the rice bacterial blight disease resistance gene xa21 in transgenic rice. Lin et al. (1995) have reported the expression of a chitinase gene in transgenic rice plants which showed resistance to the rice sheath blight pathogen, *R. solani*.

Most approaches have been marginally successful. Clearly, additional transgenic approaches using other antimicrobial genes would be useful.

VIII. Transgenes.

Genes successfully introduced into plants using recombinant DNA methodologies include, but are not limited to, those coding for the following traits: seed storage proteins, including modified 7S legume seed storage proteins (U.S. Pat. Nos. 5,508,468, 5,559,223 and 5,576,203); herbicide tolerance or resistance (U.S. Pat. Nos. 5,498,544 and 5,554, 798; Powell et al., *Science* 232:738-743 (1986); Kaniewski et al., *Bio/Tech.* 8:750-754 (1990); Day et al., *Proc. Natl. Acad. Sci. USA* 88:6721-6725 (1991)); phytase (U.S. Pat. No. 5,593,963); resistance to bacterial, fungal, nematode and insect pests, including resistance to the lepidoptera insects conferred by the Bt gene (U.S. Pat. Nos. 5,597,945 and 5,597, 946; Hilder et al., *Nature* 330:160-163; Johnson et al., *Proc. Natl. Acad. Sci. USA,* 86:9871-9875 (1989); Perlak et al., *Bio/Tech.* 8:939-943 (1990)); lectins (U.S. Pat. No. 5,276, 269); and flower color (Meyer et al., *Nature* 330:677-678 (1987); Napoli et al., *Plant Cell* 2:279-289 (1990); van der Krol et al., *Plant Cell* 2:291-299 (1990)).

IX. Expression Units to Express Exogenous DNA in a Plant.

The present invention further provides host cells transformed with a nucleic acid molecule that encodes a protein of the present invention. The host cell can be either prokaryotic or eukaryotic. Eukaryotic cells useful for expression of a protein of the invention are not limited, so long as the cell line is compatible with cell culture methods and compatible with the propagation of the expression vector and expression of the gene product. Preferred eukaryotic host cells include any plant species.

Any prokaryotic host can be used to express a rDNA molecule encoding a protein of the invention. The preferred prokaryotic host is *E. coli*.

Transformation of appropriate cell hosts with a rDNA molecule of the present invention is accomplished by well known methods that typically depend on the type of vector used and host system employed. With regard to transformation of prokaryotic host cells, electroporation and salt treatment methods are typically employed, see, for example, Cohen et al., (1972) *Proc. Natl. Acad. Sci. USA* 69, 2110-2114; and Maniatis et al., (1982) *Molecular Cloning—A Laboratory Manual,* Cold Spring Harbor Laboratory Press. With regard to transformation of vertebrate cells with vectors containing rDNAs, electroporation, cationic lipid or salt treatment methods are typically employed, see, for example, Graham et al., (1973) *Virology* 52, 456-467; and Wigler et al., (1979) *Proc. Natl. Acad. Sci. USA* 76, 1373-1376.

Successfully transformed cells, i.e., cells that contain a rDNA molecule of the present invention, can be identified by well known techniques including the selection for a selectable marker. For example, cells resulting from the introduction of an rDNA of the present invention can be cloned to produce single colonies. Cells from those colonies can be harvested, lysed and their DNA content examined for the presence of the rDNA using a method such as that described by Southern, (1975) *J. Mol. Biol.* 98, 503-517; or Berent et al., (1985) *Biotech. Histochem.* 3, 208; or the proteins produced from the cell assayed via an immunological method.

As provided herein elsewhere, several embodiments of the present invention employ expression units (or expression vectors or systems) to express an exogenously supplied nucleic acid sequence, such as the sequence coding for PINA and PINB protein in a plant. Methods for generating expression units/systems/vectors for use in plants are well known in the art and can readily be adapted for use in expressing the puroindoline proteins in a plant cell. A skilled artisan can readily use any appropriate plant/vector/expression system in the present methods following the outline provided herein.

The expression control elements used to regulate the expression of the protein can either be the expression control element that is normally found associated with the coding sequence (homologous expression element) or can be a heterologous expression control element. A variety of homologous and heterologous expression control elements are known in the art and can readily be used to make expression units for use in the present invention. Transcription initiation regions, for example, can include any of the various opine initiation regions, such as octopine, mannopine, nopaline and the like that are found in the Ti plasmids of *Agrobacterium tumefaciens*. Alternatively, plant viral promoters can also be used, such as the cauliflower mosaic virus 35S promoter to control gene expression in a plant. Lastly, plant promoters such as prolifera promoter, fruit-specific promoters, Ap3 promoter, heat shock promoters, seed-specific promoters, etc. can also be used. The most preferred promoters will be most active in seedlings.

Either a constitutive promoter (such as the CaMV or Nos promoter), an organ-specific promoter (such as the E8 promoter from tomato) or an inducible promoter is typically ligated to the protein or antisense encoding region using standard techniques known in the art. The expression unit may be further optimized by employing supplemental elements such as transcription terminators and/or enhancer elements.

Thus, for expression in plants, the expression units will typically contain, in addition to the protein sequence, a plant promoter region, a transcription initiation site and a transcription termination sequence. Unique restriction enzyme sites at the 5' and 3' ends of the expression unit are typically included to allow for easy insertion into a preexisting vector.

In the construction of heterologous promoter/structural gene or antisense combinations, the promoter is preferably positioned about the same distance from the heterologous transcription start site as it is from the transcription start site in its natural setting. As is known in the art, however, some variation in this distance can be accommodated without loss of promoter function.

In addition to a promoter sequence, the expression cassette can also contain a transcription termination region downstream of the structural gene to provide for efficient termination. The termination region may be obtained from the same gene as the promoter sequence or may be obtained from different genes. If the mRNA encoded by the structural gene is to be efficiently processed, DNA sequences which direct polyadenylation of the RNA are also commonly added to the vector construct. Polyadenylation sequences include, but are not limited to the *Agrobacterium* octopine synthase signal (Gielen et al., *EMBO J*3: 835-846 (1984)) or the nopaline synthase signal (Depicker et al., *Mol. and Appl. Genet* 1: 561-573 (1982)).

The resulting expression unit is ligated into or otherwise constructed to be included in a vector which is appropriate for higher plant transformation. The vector will also typically contain a selectable marker gene by which transformed plant cells can be identified in culture. Usually, the marker gene will encode antibiotic resistance. These markers include resistance to G418, hygromycin, bleomycin, kanamycin, and gentamicin. After transforming the plant cells, those cells having the vector will be identified by their ability to grow on a medium containing the particular antibiotic. Replication sequences, of bacterial or viral origin, are generally also included to allow the vector to be cloned in a bacterial or phage host, preferably a broad host range prokaryotic origin of replication is included. A selectable marker for bacteria should also be included to allow selection of bacterial cells bearing the desired construct. Suitable prokaryotic selectable markers also include resistance to antibiotics such as kanamycin or tetracycline.

Other DNA sequences encoding additional functions may also be present in the vector, as is known in the art. For instance, in the case of *Agrobacterium* transformations, T-DNA sequences will also be included for subsequent transfer to plant chromosomes.

The pinA and pinB sequences utilized in the present invention can also be fused to various other nucleic acid molecules such as Expressed Sequence Tags (ESTs), epitopes or fluorescent protein markers.

ESTs are gene fragments, typically 300 to 400 nucleotides in length, sequenced from the 3' or 5' end of complementary-DNA (cDNA) clones. Nearly 30,000 *Arabidopsis thaliana* ESTs have been produced by a French and an American consortium (Delseny et al., *FEBS Lett.* 405(2):129-132 (1997); *Arabidopsis thaliana* Database, http://genome.www-.stanford.edu/*Arabidopsis*). For a discussion of the analysis of gene-expression patterns depression patterns derived from large EST databases, see, e.g., M. R. Fannon, *TIBTECH* 14:294-298 (1996).

Biologically compatible fluorescent protein probes, particularly the self-assembling green fluorescent protein (GFP) from the jellyfish *Aequorea victoria*, have revolutionized research in cell, molecular and developmental biology because they allow visualization of biochemical events in living cells (Murphy et al., *Curr. Biol.* 7(11):870-876 (1997); Grebenok et al., *Plant J.* 11(3):573-586 (1997); Pang et al., *Plant Physiol.* 112(3) (1996); Chiu et al., *Curr. Biol.* 6(3): 325-330 (1996); Plautz et al., *Gene* 173(1):83-87 (1996); Sheen et al., *Plant J.* 8(5):777-784 (1995)).

Site-directed mutatgenesis has been used to develop a more soluble version of the codon-modified GFP call soluble-modified GFP (smGFP). When introduced into *Arabidopsis*, greater fluorescence was observed when compared to the codon-modified GFP, implying that smGFP is 'brighter' because more of it is present in a soluble and functional form (Davis et al., *Plant Mol. Biol.* 36(4):521-528 (1998)). By fusing genes encoding GFP and beta-glucuronidase (GUS), researchers were able to create a set of bifunctional reporter constructs which are optimized for use in transient and stable expression systems in plants, including *Arabidopsis* (Quaedvlieg et al., *Plant Mol. Biol.* 37(4):715-727 (1998)).

Berger et al. (*Dev. Biol.* 194(2):226-234 (1998)) report the isolation of a GFP marker line for *Arabidopsis* hypocotyl epidermal cells. GFP-fusion proteins have been used to localize and characterize a number of *Arabidopsis* genes, including geranylgeranyl pyrophosphate (GGPP) (Zhu et al., *Plant Mol. Biol.* 35(3):331-341 (1997)).

X. Breeding Methods.

Open-Pollinated Populations. The improvement of open-pollinated populations of such crops as rye, many maizes and sugar beets, herbage grasses, legumes such as alfalfa and clover, and tropical tree crops such as cacao, coconuts, oil palm and some rubber, depends essentially upon changing gene-frequencies towards fixation of favorable alleles while maintaining a high (but far from maximal) degree of heterozygosity. Uniformity in such populations is impossible and trueness-to-type in an open-pollinated variety is a statistical feature of the population as a whole, not a characteristic of individual plants. Thus, the heterogeneity of open-pollinated populations contrasts with the homogeneity (or virtually so) of inbred lines, clones and hybrids.

Population improvement methods fall naturally into two groups, those based on purely phenotypic selection, normally called mass selection, and those based on selection with progeny testing. Interpopulation improvement utilizes the concept of open breeding populations; allowing genes for flow from one population to another. Plants in one population (cultivar, strain, ecotype, or any germplasm source) are crossed either naturally (e.g., by wind) or by hand or by bees (commonly *Apis mellifera* L. or *Megachile rotundata* F.) with plants from other populations. Selection is applied to improve one (or sometimes both) population(s) by isolating plants with desirable traits from both sources.

There are basically two primary methods of open-pollinated population improvement. First, there is the situation in which a population is changed en masse by a chosen selection procedure. The outcome is an improved population which is indefinitely propagable by random-mating within itself in isolation. Second, the synthetic variety attains the same end result as population improvement but is not itself propagable as such; it has to be reconstructed from parental lines or clones. These plant breeding procedures for improving open-pollinated populations are well known to those skilled in the art and comprehensive reviews of breeding procedures routinely used for improving cross-pollinated plants are provided in numerous texts and articles, including: Allard, *Principles of Plant Breeding*, John Wiley & Sons, Inc. (1960); Simmonds, *Principles of Crop Improvement*, Longman Group Limited (1979); Hallauer and Miranda, *Quantitative Genetics in Maize Breeding*, Iowa State University Press (1981); and, Jensen, *Plant Breeding Methodology*, John Wiley & Sons, Inc. (1988).

Mass Selection. In mass selection, desirable individual plants are chosen, harvested, and the seed composited without progeny testing to produce the following generation. Since selection is based on the maternal parent only, and their is no control over pollination, mass selection amounts to a form of random mating with selection. As stated above, the purpose of mass selection is to increase the proportion of superior genotypes in the population.

Synthetics. A synthetic variety is produced by crossing inter se a number of genotypes selected for good combining ability in all possible hybrid combinations, with subsequent maintenance of the variety by open pollination. Whether parents are (more or less inbred) seed-propagated lines, as in some sugar beet and beans (*Vicia*) or clones, as in herbage grasses, clovers and alfalfa, makes no difference in principle. Parents are selected on general combining ability, sometimes by test crosses or topcrosses, more generally by polycrosses. Parental seed lines may be deliberately inbred (e.g. by selfing or sib crossing). However, even if the parents are not deliberately inbred, selection within lines during line maintenance will ensure that some inbreeding occurs. Clonal parents will, of course, remain unchanged and highly heterozygous.

Whether a synthetic can go straight from the parental seed production plot to the farmer or must first undergo one or two cycles of multiplication depends on seed production and the scale of demand for seed. In practice, grasses and clovers are generally multiplied once or twice and are thus considerably removed from the original synthetic.

While mass selection is sometimes used, progeny testing is generally preferred for polycrosses, because of their operational simplicity and obvious relevance to the objective, namely exploitation of general combining ability in a synthetic.

The number of parental lines or clones that enter a synthetic vary widely. In practice, numbers of parental lines range from 10 to several hundred, with 100-200 being the average. Broad based synthetics formed from 100 or more clones would be expected to be more stable during seed multiplication than narrow based synthetics.

Hybrids. A hybrid is an individual plant resulting from a cross between parents of differing genotypes. Commercial hybrids are now used extensively in many crops, including corn (maize), sorghum, sugarbeet, sunflower and broccoli. Hybrids can also be produced in wheat and rice. Hybrids can be formed a number of different ways, including by crossing two parents directly (single cross hybrids), by crossing a single cross hybrid with another parent (three-way or triple cross hybrids), or by crossing two different hybrids (four-way or double cross hybrids).

Strictly speaking, most individuals in an outbreeding (i.e., open-pollinated) population are hybrids, but the term is usually reserved for cases in which the parents are individuals whose genomes are sufficiently distinct for them to be recognized as different species or subspecies. Hybrids may be fertile or sterile depending on qualitative and/or quantitative differences in the genomes of the two parents. Heterosis, or hybrid vigor, is usually associated with increased heterozygosity which results in increased vigor of growth, survival, and fertility of hybrids as compared with the parental lines which were used to form the hybrid. Maximum heterosis is usually achieved by crossing two genetically different, highly inbred lines.

The production of hybrids is a well-developed industry, involving the isolated production of both the parental lines and the hybrids which result from crossing those lines. For a detailed discussion of the hybrid production process, see, e.g., Wright, *Commercial Hybrid Seed Production* 8:161-176, In *Hybridization of Corp Plants*, supra.

Materials and Methods

I. Disease Induction.

Rice Blast. The inoculum was prepared by placing mycelial bits of a monoconidial isolate of *Magnaporthe grisea* on Prune agar plates. The agar plates were incubated at 27 C. for 7 days. After the fungus had grown on the surface of the medium fully, the surface of the mycelium was scraped with a rubber policeman and the plates were exposed to fluorescent light for 3 days before harvesting conidia for inoculum.

Conidia were gently scraped by pouring sterile distilled water and the conidial suspension was filtered through four layers of cheese cloth. The conidial concentration was measured with a haemocytometer and adjusted by diluting with 1% gelatin solution to obtain a final concentration of 50,000 conidia per ml in 0.5% gelatin.

The inoculum was sprayed with automizer on about 20 day old rice plants. The plants were maintained in mist chamber at 90% relative humidity and 20-22 C. with 16 h fluorescent light and 8 h dark.

Sheath Blight of Rice. Individual rice plants were inoculated with *R. solani* by placing an agar block (~0.5 cm$^2$) containing the mycelium on the surface of sheath and plants were maintained in growth chamber with high humidity.

Common Bunt. Seedlings of the control cultivar 'Bobwhite' and the two transgenic lines were inoculated with *Tilletia tritici* teliospores as previously described for covered smut of barley (Willits and Sherwood. 1999. *Phytopathology* 89:212-217).

Dwarf Bunt. The spores are incubated at 8° C. for 2 weeks before inoculating the seeds as described above for common bunt. The plants are incubated at 8° C. for 1 month before transferring to normal growth conditions.

Bacterial Spot Disease. The inoculation of tomato plants with *Xanthomonas campestris pv. vesicatoria* (Xcv) may be conducted according to Lund et al. (1998, *Plant Cell* 10(3): 371-382); Jones et al., 1998, *Phytopathology* 88(1):33-38; Scott et al., 1997, *HortScien Phytopathology ce* 32(4):724-727; Scott et al., 1995, *HortScience* 30(3):579-581; and Wang et al., 1994, 84(7):702-706.

Tomato Leaf Mold caused by *Cladosporium fulvum*. The inoculation of tomato plants with *C. fulvum* may be conducted according to Spanu, 1998, *Physiological and Molecular Plant Pathology* 52(5):323-334; Lam et al., 1998, *Physiological and Molecular Plant Pathology* 52(5):309-321; Lauge et al., 1997, *Molecular Plant-Microbe Interactions* 10(6):725-734; and Xing et al., *The Plant Cell* 9(2):249-259.

II. Disease Scoring.

Rice Blast. Leaf blast was scored 7 days after pathogen inoculation. For leaf blast scoring, number of leaves with disease score 1, 2, 3 . . . 9 were determined using the 0-9 scale of the Standard Evaluation System developed by International Rice Research Institute (IRRI). According to blast lesion size, 0-3 scale rating are resistant and 4-9 are susceptible.

Sheath Blight of Rice. The sheath blight symptoms caused by *R. solani* fungal infection were scored 6 days after pathogen inoculation by measuring total lesion height and total plant height. The following formulas were calculated based on this information:

Percent disease incidence=(lesion height/plant height)×100.

Percent disease suppression=((100−treatment)/control))×100.

Common and Karnal Bunt. The wheat spikes are inspected for spores. The percentage of infected wheat heads is recorded.

Bacterial Spot Disease. The tomato seeds/seedlings/plants are inspected for disease symptoms (i.e., lesions) and scored for foliar disease development according to Lund et al. (1998, *Plant Cell* 10(3):371-382); Jones et al., 1998, *Phytopathology* 88(1):33-38; Scott et al., 1997, *HortScien* 32(4):724-727;

Scott et al., 1995, *HortScience* 30(3):579-581; and Wang et al., 1994, *Phytopathology* 84(7):702-706.

Tomato Leaf Mold caused by *Cladosporium fulvum*. The tomato plants may be scored for disease according to Spanu, 1998, *Physiological and Molecular Plant Pathology* 52(5): 323-334; Lam et al., 1998, *Physiological and Molecular Plant Pathology* 52(5):309-321; Lauge et al., 1997, *Molecular Plant-Microbe Interactions* 10(6):725-734; Xing et al., *The Plant Cell* 9(2):249-259; and Honee et al., 1995, *Plant Mol. Biol.* 29(5):909-920. Scoring may be based on the number and magnitude of necrotic lesions/flecks/spots; percentage of dead seedlings/plants, delayed growth, and/or degree of leaf desiccation and abscission.

III. Production of Transgenic Plants.

Vectors according to the invention may be used to transform plants as desired, to make plants according to the invention as discussed elsewhere herein.

Rice Transformation. The methods described by Sivamani et al. (1996) has been adopted for transforming rice cultivar 'M202' (Johnson et al. 1986). The technique as routinely practiced initially utilizes embryogenic calli cultured from mature seeds.

The Biolistic PDS-1000 He (Bio-Rad laboratories, USA) device was used for transforming the rice tissues via microprojectile bombardment.

For rice calli 1500 psi rupture discs were used. Other procedures such as sterilization of the rupture discs, macrocarriers, stopping screens etc., were strictly in accordance with the manufacturer's manual.

Wheat Transformation. The methods described by Weeks et al. (1993) and Vasil et al. (1993) have been adopted with minor modifications for transforming the wheat cultivar 'Bobwhite'. The technique as routinely practiced initially utilizes immature embryos isolated from wheat cultivars approximately 7 days post anthesis.

The Biolistic PDS-1000 He (Bio-Rad laboratories, USA) device was used for transforming the wheat tissues via microprojectile bombardment.

For wheat calli 1500 psi rupture discs were used. Other procedures such as sterilization of the rupture discs, macrocarriers, stopping screens etc., were strictly in accordance with the manufacturer's manual.

Tomato Transformation. Dicotyledonous plants, such as the tomato, may also transformed to produce plants transgenic for one or more of the puroindoline genes.

For example, tomato plants may be transformed using Ti plasmid technology, for example as described by Bevan (1984) *Nucleic Acids Research* 12:8711-721 and U.S. Pat. No. 5,141,870. For additional information on the transformation of tomato plants, see, for example, McGurl et al., 1994, *Proc. Natl. Acad. Sci. USA* 91(21):9799-9802; Tieman et al., 1992, *Plant Cell* 4:667-679; and McGarvey et al., 1995, *Biotechnology* 13(13):1484-1487.

As a specific example, transgenic tomato plants can be produced using the binary vector pAGS152 in *A. tumefaciens* strain LBA4404, wherein the vector contains one or more of the puroindoline genes (U.S. Pat. No. 5,141,870, hereby incorporate by reference in its entirety).

IV. Plasmids.

The plasmid DNA pRQ101 containing the coding sequence of the Bar gene (Fromm et al., 1990) under control of the CaMV 35S promotor with AdhI intron and NOS terminator (Sivamani et al., M.S. Thesis in preparation) was used as selectable marker for selecting transgenic wheat tissue.

As a selectable marker for rice, the plasmid DNA pILTAB222 containing the coding sequence of the hygromycin B phosphotransferase under the control of the maize ubiquitin promoter was used (Sivamani et al. 1996).

For the introduction of the puroindoline genes the plasmid DNAs pPuroA containing the pinA gene and the plasmid pPuroB containing the pinB gene were created. Both plasmids pPuroA and pPuroB are under the control of the maize ubiquitin promoter (Christensen et al. 1996) and NOS terminator (Rogers et al. 1987).

These plasmids were constructed using the intact pinA or pinB coding sequence. Constructs include transit peptides and consensus start site.

Primers used for amplifying pinA coding sequences using the RT-PCR technique were

```
                                             (SEQ ID NO. 1)
PA5BH (5' CGGGATCCAACAATGAAGGCCCTCTTCCTCATAGG 3')
and
                                             (SEQ ID NO. 2)
PA3BH (5' GGATCCCGCCAGTAATAGCCAATAGTGCCGGGGAT 3').
```

Primers used for amplifying pinB coding sequences using the RT-PCR technique were

```
                                             (SEQ ID NO. 3)
PB5BH (5' CGGGATCCAACAATGAAGACCTTATTCCTCCTAGC 3')
and
                                             (SEQ ID NO. 4)
PA3BH (5' GGATCCCGCCAGTAATAGCCACTAGGGAACTT 3').
```

A sample of RNA prepared from the variety 'Chinese Spring' was used as source material for the RT-PCR reaction as per standard techniques. The amplified genes were digested by BamHI and ligated into a vector downstream of the ubiquitin promoter. The ubiquitin promoter construct had been previously digested with BamHI and phosphatase treated to prevent self ligation. pPuroA and pPuroB plasmids used in transformation experiments were verified by standard sequencing techniques to assure no errors had occurred in the PCR amplification.

V. Selection and Regeneration of Transgenic Plants.

Rice and Wheat. Transgenic rice plants were obtained from the bombarded embryogenic calli of rice by the technique of Sivamani et al. (1996) using hygromycin selection.

Transgenic wheat plants were obtained from bombarded immature embryos by the methods described by Weeks et al. (1993) and Vasil et al. (1993) using bialaphos (Meiji Seika Kaisha Ltd, Japan) selection.

The resistant calli of rice and wheat were transferred to medium to induce production of both shoots and roots. Putative transgenic plantlets were transferred to the greenhouse and allowed to self-fertilize. For wheat, typically more than 75% of these plantlets are escapes and true transgenic plants were selected by spraying the plants with 0.1% glufosinate (Liberty®, Agrevo Inc.).

Tomato. Transgenic tomato plants can be obtained by agroinoculation by the technique of Day et al. (1991, *Proc. Natl. Acad. Sci. USA* 88(15):6721-6725) using hygromycin selection. Alternative methods of selecting the transformed tomato plants include kanamycin resistance selection and xylose isomerase selection (Haldrup et al., 1998, *Plant Mol. Biol.* 37(2):287-296).

EXAMPLES

Example 1

Analysis of Transgenic Plants.

The initial pool of wheat and rice transformants yielded a number of independent transformants. The T0 plants were allowed to set seed and mature in the greenhouse or growth chambers under controlled conditions.

T1 segregation data for hygromycin or basta resistance demonstrated that all transgenic events exhibited a 3:1 segregation pattern consistent with a single locus.

Example 2

PCR, Hygromycin Resistance Segregation, and Apparent Copy Number of Selected Lines of Transgenic Rice.

The selected rice transformants were analyzed by PCR for the presence of the introduced transgene (Table I), for T1 seed segregation data for hygromycin resistance, and for apparent copy number via analysis of southern blots.

PCR screening of transgenic rice plants utilized PA5BH and PA3BH (primer sequences given above) for the presence of pinA and PB5BH and PB3BH (primer sequences given above) for the presence of pinB in genomic DNA samples prepared from leaf tissue using standard PCR protocols.

Amplification of 'M202' genomic DNA using either primer pair does not give a reaction. 'Line 97-3', which is hygromycin resistant, also is PCR negative for the presence of pinA and pinB. 'Line 91-29' is pinA positive and pinB negative. 'Line 97-5' is pinA negative and pinB positive. 'Line 97-1' is PCR positive for both pinA and pinB.

Chi-square values obtained using T1 seed segregation data from each of the four transgenic rice lines are not inconsistent with 3:1 segregation. This indicates that in all likelihood the introduced transgene(s) reside together at a single locus. Apparent number of introduced copies of pinA and/or pinB ranged from 0-4.

TABLE I

PCR, Hygromycin resistance segregation, and apparent copy number of selected lines of transgenic rice.

| Plant[1] | PCR[2] PinA/PinB | Segregation[3] Resistant/ Susceptible | chi-square (3:1) | Apparent Copy Number[4] PinA/PinB |
|---|---|---|---|---|
| M202 Control | −/− |  |  | 0/0 |
| 97-3 | −/− | 34/11 | 0.0074 | 0/0 |
| 91-29 | +/− | 37/8 | 1.25 | 4/0 |
| 97-5 | −/+ | 34/12 | 0.029 | 0/2 |
| 97-1 | +/+ | 35/15 | 0.67 | 3/3 |

[1]All plants are derivatives of rice variety 'M202'. '97-3' was transformed only with the vector containing the hygromycin resistance gene (pILTAB222). The other plants were transformed with pinA, pinB or both.
[2]PCR screening was performed using pinA or pinB specific primer pairs on samples of genomic DNA.
[3]T1 segregation data represents hygromycin selection for transformed tissue. T1 seeds were surface sterilized and germinated on agar plates containing hygromycin. Plants that showed few or no adverse symptoms were scored as resistant and susceptible plants were those that did not survive.
[4]To estimate copy number, genomic DNA from each line was digested with an appropriate restriction enzyme, electrophoresed, blotted to a nylon membrane, and probed with either pinA or pinB as per standard techniques. Copy number estimate is based on the number of hybridizing fragments of DNA.

Example 3

Transcript Expression Data of pinA and pinB in Transgenic Rice.

Expression analyses of pinA and pinB were carried out on the transgenic lines of rice using standard techniques for Northern blot analysis (Table II).

A line classified as positive demonstrated significant levels of transcript detected. Control cultivar 'M202' (i.e., the corresponding non-transgenic line) and 'Line 97-3' were found to have no expression of either pinA or pinB in any of the tissues sampled. 'Line 91-29' was positive for pinA expression in leaf and endosperm tissue. 'Line 97-5' was positive for pinB expression in both leaf and endosperm tissue and 'Line 97-1' was positive for both pinA and pinB in leaf, endosperm, and root tissue.

TABLE II

Transcript expression data of pinA and pinB in transgenic rice.

| Plant[1] | Leaf PinA/PinB | Northern Analysis[2] Endosperm PinA/PinB | Root PinA/PinB |
|---|---|---|---|
| M202 Control | −/− | −/− | −/− |
| 97-3 | −/− | −/− | −/− |
| 91-29 | +/− | +/− | ND |
| 97-5 | −/+ | −/+ | ND |
| 97-1 | +/+ | +/+ | +/+ |

[1]All plants are derivatives of rice variety 'M202'. '97-3' was transformed with the vector (pITLTAB222). The other plants were transformed with PinA, PinB or both.
[2]Northern Analysis was performed on total RNA extracted from leaves, developing seeds, or roots of transgenic plants as per standard protocols.

Example 4

Increased Tolerance of Transgenic Rice to *Rhizoctonia solani*.

Inoculation and disease scoring were performed as explained previously.

Experiments indicate that rice containing either pinA or pinB has greater tolerance/resistance to *R. solani* (sheath blight)(Table III).

The apparent level of protection in these transgenic plants ranges from 2-40%. Control transformed rice without expression of either PINA or PINB did not differ significantly from 'M202'. The original, non-transformed (i.e., non-transgenic) 'M202' line is also referred to as the "corresponding non-transgenic line".

Transgenic rice 'Line 91-29' with pinA expression exhibited a roughly 8-31% reduction in disease severity, while expression of pinB in 'Line 97-5' reduced severity by 2-23%. Expression of both puroindolines in 'Line 97-1' gave the greatest suppression, 16-40%.

TABLE III

Increased tolerance of transgenic rice to *Rhizoctonia solani* (sheath blight).

| Plant[1] | Experiment 1 Disease Incidence | Percent Control | Experiment 2 Disease Incidence | Percent Control[2] |
|---|---|---|---|---|
| M202 Control | 30.25 | 0 | 23.13 | 0 |
| 97-3 (pinA− pinB−) | 28.52 | 5.7 | 21.75 | 5.97 |

TABLE III-continued

Increased tolerance of transgenic rice to Rhizoctonia solani (sheath blight).

| Plant[1] | Experiment 1 Disease Incidence | Percent Control | Experiment 2 Disease Incidence | Percent Control[2] |
|---|---|---|---|---|
| 91-29 (pinA+ pinB−) | 27.82 | 8.0 | 17.87 | 30.96 |
| 97-5 (pinA− pinB+) | 29.60 | 2.2 | 15.97 | 22.74 |
| 97-1 (pinA+ pinB+) | 25.41 | 16.0 | 13.88 | 39.99 |

[1]All plants are derivatives of rice variety M202. 97-3 was transformed with the vector (pILTAB222). The other plants were transformed with PinA, PinB or both.
[2]Rhizoctonia solani inoculations were carried out according to standard protocols. Percent control is a simple comparison of disease incidence between transgenic line and untransformed control M202.

Example 5

Increased Tolerance of Pin-Transformed Rice to Rice Blast.

Inoculation and disease scoring were performed as explained previously.

In transgenic 'Line 91-29' (pinA+) disease reduction ranged from 5-25.5% (Table IV.)

Expression of pinB in 'Line 97-5' exhibited disease reduction of between 20 and 29% and expression of both pinA and pinB in 'Line 97-1' gave disease reduction between 47.5 and 56.3%.

TABLE IV

Increased tolerance of Pin-transformed rice to Magnaporthe grisea (rice blast).

| Plant[1] | Number of leaves | Disease score[2] | % Disease Reduction |
|---|---|---|---|
| Experiment 1 | | | |
| M202 Control | 14 | 71.4 | |
| 97-3 (pinA− pinB−) | 14 | 78.6 | 0 |
| 91-29 (pinA+ pinB−) | 12 | 67.7 | 5.2 |
| 97-5 (pinA− pinB+) | 14 | 57.1 | 20.0 |
| 97-1 (pinA+ pinB+) | 16 | 37.5 | 47.5 |
| Experiment 2 | | | |
| M202 Control | 71 | 54.9 | |
| 97-3 (pinA− pinB−) | 37 | 54.1 | 1.5 |
| 91-29 (pinA+ pinB−) | 22 | 40.9 | 25.5 |
| 97-5 (pinA− pinB+) | 82 | 39.0 | 29.0 |
| 97-1 (pinA+ pinB+) | 50 | 24.0 | 56.3 |

[1]All plants are derivatives of rice variety 'M202'. PinA− PinB− was transformed with the vector (pILTAB222). The other plants were transformed with PinA, PinB or both.
[2]Disease score is calculated as the number of leaves with an IRRI score of 4-9 divided by the total number of leaves. Leaves with IRRI disease scores of 0-3 are counted as resistant.

Example 6

Production of Transformed Rice Plants Using Conventional Plant Breeding.

Transgenic rice 'Line 97-1' (pinA+pinB+) plants are sexually crossed to a different rice line, cultivar or variety of rice plants and the resultant seed is harvested. The harvested seed is planted and the seedlings are grown.

The transcript expression data of pinA and pinB are determined as set forth in Example 2 and the lines transgenic for pinA, pinB and/or both pinA and pinB are selected.

Alternatively, or in addition, the segregating lines are tested for their tolerance/resistance to R. solani and/or M. grisea as set forth in Examples 3 and 4, respectively.

The selected transformed seedlings are grown to maturity and the resultant selfed seed is harvested and bulked to produce bulked transgenic seed for planting as a rice crop plant.

Alternatively, the mature transformed plants are crossed to a different rice line (a sister line or a different variety) to produce hybrid seed. The resultant hybrid seed is bulked and used to produce a hybrid rice crop.

As discussed above, numerous variations on these breeding schemes are possible. For example, the originally obtained transformed seedlings may be selfed for one or several generations before being used for the production of either selfed or hybrid seed production. For a discussion of rice production methods, see Langer et al., 1991, Agricultural Plants, Second Edition, Cambridge University Press and Coffman et al., 1980, Chapter 36, In Hybridization of Crop Plants, The American Society of Agronomy, Inc., Madison, Wis. For a discussion on various practical aspects of rice breeding, see Coffman and Herrera, 1980, Rice, In Hybridization of Crop Plants, Fehr and Hadley, eds; Ch.36:511-522, American Society of Agronomy.

Example 7

PinA and pinB PCR Results and Glufosinate Resistance Segregation Information for Selected Lines of Transgenic Wheat.

The two available transgenic lines of wheat variety 'Bobwhite' were screened for the presence of the introduced pinA sequences via PCR on samples of genomic DNA.

Screening for the presence of the pinA sequence utilized 5' primer PA5BH, described above, and a NOS specific primer based on the NOS terminator (Rogers et al. 1987).

'Line 84' was PCR positive for the presence of pinA and line 67 for pinB (Table V). Both of these transgenic lines were screened for T1 transgene segregation by herbicide selection using a solution of 0.1% glufosinate (Liberty®, Agrevo, Inc.) on plants arising from T1 seed.

Both 'Line 84' and 'Line 67' segregated herbicide resistant: susceptible in a 3:1 ratio indicating a single locus in both lines contained both the BAR gene and the introduced puroindoline.

TABLE V

PinA and pinB PCR results and glufosinate resistance segregation information for selected lines of transgenic wheat.

| Plant[1] | PCR[2] pinA/pinB | Segregation[3] Resistant/ Susceptible | chi-square (3:1) |
|---|---|---|---|
| Bobwhite | −/− | | |
| Line 84 | +/− | 43/15 | 0.023 |
| Line 67 | −/+ | 74/21 | 0.426 |

[1]All plants are derivatives of wheat variety 'Bobwhite'. '84' was transformed with the PinA vector and 67 with PinB.
[2]PCR screening was performed using pinA or pinB transgene specific primer pairs on samples of genomic DNA.
[3]T1 segregation data represents hygromycin selection for transformed tissue. T1 seeds were germinated in soil and allowed to grow for two weeks. All plants were then treated with a solution of 0.1% glufosinate. Plants that showed few or no adverse symptoms were scored as resistant and susceptible plants were those that did not survive.

Example 8

Transcript Expression Data of pinA and pinB in Transgenic Wheat.

Expression data of pinA and pinB was carried out on the transgenic lines of wheat using standard techniques for Northern blot analysis (Table VI).

A line classified as positive demonstrated significant levels of transcript detected. Control cultivar 'Bobwhite' has no expression of either pinA or pinB in the leaf tissues sampled. 'Line 84' was positive for pinA expression in leaf tissue and 'Line 67' was positive for pinB expression in leaf tissue.

TABLE VI

Transcript expression data of pinA and pinB in transgenic wheat.

| Plant[1] | Northern Analysis[2] Leaf PinA/PinB |
|---|---|
| Bobwhite | −/− |
| Line 84 | +/− |
| Line 67 | −/+ |

[1] All plants are derivatives of wheat variety 'Bobwhite'. 'Line 84' was transformed with the PinA vector and 67 with PinB.
[2] Northern Analysis was performed on total RNA extracted from leaves of transgenic plants as per standard protocols.

Example 9

Increased Tolerance of Transgenic 'Bobwhite' Wheat Plants to Common Bunt.

Inoculation and disease scoring were performed as explained previously.

PinA positive 'Line 84' had a percent disease reduction versus control of 33-80% and pinB positive 'Line 67' had disease reduction of 33-100% (see Table VII).

Example 10

Production of Transgenic Wheat Plants Using Conventional Plant Breeding.

'Line 84' (pinA+pinB−) is crossed to 'Line 67' (pinA−pinB+) and progeny which are pinA+ pinB+ are identified by PCR as described previously.

The selected pinA+ pinB+ progeny, 'Bobwhite', 'Line 84' and 'Line 64' are all tested for tolerance to common bunt, dwarf bunt and/or karnal bunt as described previously.

For each disease tested, the percentage disease reduction is as follows:

pin*A*+pin*B*+>pin*A*+pin*B*− or pin*A*−pin*B*+>> 'Bobwhite'.

Thus, the combination of pinA+ and pinB+ has an additive or synergistic effect as regards the ability of the plants to tolerate each of the diseases individually or collectively.

The selected pinA+ pinB+ lines can be used in conventional plant breeding programs to produce pinA+ pinB+ lines with any preferred wheat genotype. The desired pinA+ pinB+ plants can be identified by PCR or by using disease screening tests.

Example 11

Production of Transformed Tomato Plants.

The xylose isomerase gene (xylA) from *Thermoanaerobacterium thermosulfurogenes* (formerly *Clostridium thermosulfurogenes*), pinA and/or pin B can be transferred to 'Burpee's® Big Boy Tomato' plants by *Agrobacterium*-mediated transformation using the methods of Haldrup et al. (1998, *Plant Mol. Biol.* 37(2):287-296).

The initial pool of tomato transformants would yield a number of independent transformants. The T0 plants would be allowed to set seed and mature in the greenhouse, growth chamber or field.

TABLE VII

Increased tolerance of transgenic Bobwhite wheat plants to common bunt.

| Plant[1] | Number of Plants | % Infected Plants[2] | % Disease Reduction |
|---|---|---|---|
| Experiment 1 | | | |
| Bobwhite | 27 | 100 | |
| Line 67 (pinA− pinB+) | 9 | 60 | 40 |
| Experiment 2 | | | |
| Bobwhite | 13 | 100 | |
| Line 84 (pinA+ pinB−) | 6 | 67 | 33 |
| Line 67 (pinA− pinB+) | 12 | 67 | 33 |
| Experiment 3[3] | | | |
| Bobwhite | 13 | 15 | |
| Line 84 (pinA+ pinB−) | 29 | 3 | 80 |
| Line 67 (pinA− pinB+) | 29 | 0 | 100 |

[1] All plants are Bobwhite transformed with either pinA (Line 84 PinA+) or pinB (Line 67 PinB+). ND = Not Done.
[2] A plant with at least one bunted head was scored as infected.
[3] The number of teliospores used to inoculate seeds in Experiment 3 was lowered to reduce the percentage of infection in the control plants to levels more typically found in the field.

T1 segregation data for xylose isomerase selection would demonstrate that all transgenic events exhibited a 3:1 segregation pattern consistent with a single locus.

Example 12

PCR, Xylose Isomerase Segregation, and Apparent Copy Number of Selected Lines of Transgenic Tomato.

The xylose isomerase system enables the transgenic tomato cells to utilize xylose as a carbohydrate source. Thus, it is an example of a positive selection system because transgenic cells proliferate while non-transgenic cells are starved but still survive.

PCR screening and the determination of apparent copy number are accomplished as set forth in Example 2 for transgenic rice.

Example 13

Transcript Expression Data of pinA and pinB in Transgenic Tomato.

Expression analyses of pinA and pinB can be carried out on the transgenic lines of tomato using standard techniques for Northern blot analysis, as discussed previously herein.

Example 14

Increased Tolerance of Transgenic Tomato to Xanthomonas campestris pv. vesicatoria.

Inoculation and disease scoring were performed as explained previously.

Experiments will indicate that tomatoes containing pinA and/or pinB will have greater tolerance/resistance to the bacterial pathogen Xanthomonas campestris pv. vesicatoria than the non-transformed 'Big Boy' control plants.

Example 15

Increased Tolerance of Transgenic Tomato to Cladosporium fulvum.

Inoculation and disease scoring were performed as explained previously.

Experiments will indicate that tomatoes containing pinA and/or pinB will have greater tolerance/resistance to the bacterial pathogen Cladosporium fulvum than the non-transformed 'Big Boy' control plants.

Example 16

Production of Transformed Tomato Plants Using Conventional Plant Breeding.

The transgenic 'Big Boy' tomato plants identified in Examples 11-13 are sexually crossed to non-transgenic 'Big Boy' tomato plants (or another line, cultivar or variety of tomato plants) and the resultant seed is harvested.

The harvested seed is planted and the seedlings are evaluated for transcript expression of pinA and/or pinB and the transgenic lines are selected.

Alternatively, or in addition, the segregating lines are tested for their tolerance/resistance to the causal agent of bacterial spot disease as set forth previously.

The transformed seedlings are grown to maturity and the resultant selfed seed is harvested and bulked to produce bulked transgenic seed for planting as a tomato crop plant.

Alternatively, the mature transformed plants are crossed to a different tomato line (a sister line or a different variety) to produce hybrid seed. The resultant hybrid seed is bulked and used to produce a hybrid tomato crop.

As discussed above in the Materials and Methods, numerous variations on these breeding schemes are possible. For example, the originally obtained transformed seedlings may be selfed for one or several generations before being used for the production of either selfed or hybrid seed production. For a discussion of tomato production methods, see Langer et al., 1991, Agricultural Plants, Second Edition, Cambridge University Press.

Any tomato plants produced by any of these various breeding schemes may be tested for tolerance/resistance/susceptibility to various pathogens (e.g., X. campestris and C. fulvum) using disease inoculation and disease scoring methods well known to one in the plant pathology arts.

The foregoing detailed description has been given for clearness of understanding only and no unnecessary limitations should be understood therefrom as modifications will be obvious to those skilled in the art.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

REFERENCES FOR WENCH A COMPLETE CITATION IS NOT PROVIDED IN THE TEXT OF THE SPECIFICATION.

Agri. Research Station, Maruteru. 1986. In Sixty years of rice research at Maruteru. 73 pages.

Anon. 1988. Sheath blight : Losses cost $67 million a year. Rice J. 41:5-8.

Asuyama, H. 1965. Morphology, taxonomy, host range and life cycle of Pyricularia oryzae. pp. 9-22. In The Rice Blast Disease. Proc. Symp. IRRI. John Hopkins University Press, Baltimore, Md.

Awoderu, V. A. 1990. Yield loss attributable to neck-rot of rice caused by Pyricularia oryzae, Cav. In Dote d'Ivoire. Tropical Pest Management 36:394-396.

Baker, R. J. 1977. Inheritance of kernel hardness in spring wheat. Crop Sci. 14:960-962.

Blochet, J. E., Chevalier, C., Forest, E., Pebay-Peyroula, E., Gautier, M. F., Joudrier, P., Pezolet, M., and Marion, D. 1993. Complete amino acid sequence of puroindoline, a new basic and cystine-rich protein with a unique tryptophan-rich domain, isolated from wheat endosperm by Triton X-114 phase partitioning. FEBS 329:336-340.

Bordier, C. 1981. Phase separation of integral membrane proteins in Triton X-114 solution. J. Biological Chemistry 256:1604-1607.

Broekaert, W. F., Cammue, B. P. A., De Bolle, M. F. C., Thevissen K., De Samblanx, G. W., and Osborn, R. W. 1997. Antimicrobial peptides from plants. Crit. Rev. Plant Sci. 16:297-323.

Carmona, -M. J.; Molina, -A.; Fernandez, -J. A.; Lopez-Fando, -J. J.; Garcia-Olmedo, -F. 1993. Expression of the alpha-thionin gene from barley in tobacco confers enhanced resistance to bacterial pathogens. *Plant-J.* 3 (3): 457-462.

Christensen, A. H. and Quail, P. 1996. Ubiquitin promoter-based vectors for high-level expression of selectable and/or screenable marker genes in monocotyledonous plants. *Transgenic Res.* 5:213-218.

Dale, P. J., Irwin, J. A. and Scheffler, J. A. 1993. The experimental and commercial release of transgenic crop plants. *Plant Breeding.* 111:1-22.

Disthaporn, S. 1993. Current rice blast epidemics and their management in Thailand. International symposium on Rice Blast Disease. Univ. of Wisconsin, Madison (abstract).

Dubreil, L., Gaborit, T., Bouchet, B., Gallant, D. J., Broekaert, W. F., Quillien, L., and Marion, D. 1998. Spatial and temporal distribution of the major isoforms of puroindolines (puroindoline-a and puroindoline-b) and non specific lipid transfer protein (ns-LTPe1) of *Triticum aestivum* seeds. Relationships with their in vitro antifungal properties. *Plant Science* 138: 121-135.

Epple, P., Apel, K., and Bohlmann, H. 1997. Overexpression of an endogenous thionin enhances resistance of *Arabidopsis* against *Fusarium oxysporum. The Plant Cell* 9:509-520.

Fomba, S. N., and Taylor, D. R. 1994. Rice blast in west Africa: Its nature and control. pp. 343-355. In Rice Blast Disease. R. S. Zeigler, S. Leong, and P. S. Teng, eds. CAB International, Wallingford, U.K.

Fromm, M. E., Morrish, F. Armstrong, C. Williams, R. Thomas, J., and Klein, T. M. 1990. Inheritance and expression of chimeric genes in the progeny of transgenic maize plants. *Bio/Technology* 8:833-839.

Garcia-Olmedo, F., Molina, A., Segura, A., and Moreno, M. 1995. The defensive role of nonspecific lipid transfer proteins in plants. *Trends Microbiol.* 3:72-74.

Garnier, J., Gibrat, J. F., and Robson, B. 1996. GOR method for predicting protein secondary structure from amino acid sequence. *Meth. Enzymol.* 266:540-553.

Gatineau, E., Toma, R., Montenay-Garestier, Th., Takechi, M., Fromageot, P., and Menez, A. 1987. Role of tyrosine and tryptophan residues in the structure-activity relationships of a cardiotoxin from *Naja nigricollis* venom. *Biochemistry* 26:8046-8055.

Gautier, M. F., Aleman, M. E., Guirao, A., Marion, D., and Joudier, P. 1994. *Triticum aestivum* puroindolines, two basic cystine-rich seed proteins: cDNA analysis and developmental gene expression. *Plant Molec. Biol.* 25:43-57.

Giroux, M. J., Martin, J. M., Habernicht, D. K., Lanning, S., Hemphill, A., and Talbert, L. (2000) Association of Puroindoline Sequence Type and Grain Hardness in Hard Red Spring Wheat. *Crop Science*, in press, March April 2000 issue.

Giroux, M. J., and Morris, C. F. 1997. A glycine to serine change in puroindoline b is associated with wheat grain hardness and low levels of starch-surface friabilin. *Theor. Appl. Genet.* 95: 857-864.

Giroux, M. J., and Morris, C. F. 1998. Wheat grain hardness results from highly conserved mutations in the friabilin components puroindoline a and b. *Proc. Natl. Acad. Sci.* 95: 6262-6266.

Greenblatt, G. A., Bettge, A. D., and Morris, C. F. 1995. The relationship among endosperm texture, friabilin occurrence, and bound polar lipids on wheat starch. *Cereal Chem.* 72:172-176.

Greenwell & Schofield. 1986. *Cereal Chem.* 63:379-380.

Hill, C. P., Yee, J., Selsted, M. E., and Eisenberg, D. 1991. Crystal structure of defensin HNP-3, an amphiphilic dimer: mechanisms of membrane permeabilization. *Science* 251:1481-1485.

Hori, M. 1969. On forecasting the damage due to sheath blight o rice plants and the critical point for judging the necessity of chemical control of the disease. *Review of Plant protection Research.* 2:70-73.

Ishiguro, K. 1994. Using simulation models to explore better strategies for the management of blast disease in temperate rice pathosystems. pp. 435-449. In Rice Blast Disease. R. S. Zeigler, S. Leong, and P. S. Teng, eds. CAB International, Wallingford, U.K.

Jameson, B. A., and Wolf, H. 1988. The antigenic index: a novel algorithm for predicting antigenic determinants. *CABIOS* 4:181-186.

Johnson, C. W., Carnahan, H. L., Tseng, S. T., Oster, J. J., and Hill, J. E. 1986. Registration of 'M-202' rice. *Crop Science* 26:198.

Jolly et al. 1993. *Theor. Appl. Genet.* 86:589-597.

Kagan, B. L., Selsted, M. E., Ganz, T., and Lehrer, R. I. 1990. Antimicrobial defensin peptides form voltage-dependent ion-permeable channels in planar lipid bilayer membranes. *Proc. Natl. Acad. Sci. USA* 87:210-214.

Kauffman, H. E., Ebron, T. and Merca, S. 1977. Rice disease survey: 1975. *Int'l. Rice Res. Newsl.* 2:8-9.

Kim, C. K. 1994. Blast management in high input, high yield potential, temperature rice ecosystems. Pages 451-463, In: Rice Blast Disease. R. S. Zeigler, S. Leong, and P. S. Teng, eds. CAB International, Wallingford, U.K.

Kozaka, T. 1965. Ecology of Pellicularia sheath blight of rice plant and its chemical control. *Ann. Phytopathol. Soc. Japan.* 31:179-185.

Law, C. N., C. F. Young, J. W. S. Brown, J. W. Snape, and J. W. Worland. 1978. The study of grain protein control in wheat using whole chromosome substitution lines. pp. 483-502. In Seed protein improvement by nuclear techniques. International Atomic Energy Agency, Vienna, Austria.

Lee, F. N. 1994. Rice breeding programs, blast epidemics and blast management in the United States. pp. 489-500. In Rice Blast Disease. R. S. Zeigler, S. Leong, and P. S. Teng, eds. CAB International, Wallingford, U.K.

Lee, F. N. and Rush, M. C. 1983. Rice sheath blight: a rice disease. *Plant Disease* 67:829-832.

Lin, W., Anuratha, C. S., Datta, K., Potrykus, I., Muthukrishnan, S. and Datta, S. K. 1995. Genetic engineering of rice for resistance to sheath blight. Bio/Technology, 13:686-691.

Logemann, J., Jach, G., Tommerup, H., Mundy, J. and Schell, J. 1992. Expression of a barley ribosome-inactivating protein leads to increased fungal protection in transgenic tobacco plants. *Bio/Technology* 10:305-308.

Marion, D., Gautier, M. -F., Joudrier, P., Ptak, M., Pezolet, M., Forest, E., Clark, D. C., and Broekaert, W. 1994. Structure and function of wheat lipid binding proteins. pp. 175-180. In Wheat Kernel Proteins-Molecular and Functional Aspects. Universita degli studi della tuscia. S Martino al Cimino, Sep. 28-30, 1994. Viterbo, Italy.

Martinez-Espinoza, A. D., S. A. Gerhardt, and J. E. Sherwood. 1993. Morphological and mutational analysis of *Ustilago hordei* mating. *Exp. Mycol.* 17:200-214.

Mattern, P. J., R. Morris, J. W. Schmidt, and V. A. Johnson. 1973. Location of genes for kernel properties in the wheat cultivar 'Cheyenne' using chromosome substitution lines. pp. 703-707. In E. R. Sears, and L. M. S. Sears (ed.) Proc.

Int. Wheat Genet. Symp., 4th, Columbia, Mo. Aug. 1-6, 1973. Agric. Exp. Sta., Univ. Missouri, Columbia, Mo.

Mattern, P. J., Morris, R., Schmidt, J. W., and Johnson, V. A. 1973. In Proceedings of the 4th International Wheat Genetics Symposium, (University of Missouri, Columbia, Mo.,) pp. 703-707.

Molina, A., Diaz, I., Vasil, I. K., Carbonero, P., and Garcia-Olmedo, F. 1996. Two cold-inducible genes encoding lipid transfer protein LTP4 from barley show differential responses to bacterial pathogens. *Mol. Gen. Genet.* 252: 162-168.

Molina, A., and Garcia-Olmedo, F. 1997. Enhanced tolerance to bacterial pathogens caused by the transgenic expression of barley lipid transfer protein LTP2. *The Plant Journal* 12:669-675.

Molina, A., Segura, A. and Garcia-Olmedo, F. 1993. Lipid transfer proteins (nsLTPs) from barley and maize leaves are potent inhibitors of bacterial and fungal plant pathogens. *FEBS Letters* 316:119-122.

Morris et al. 1994. *J. Cereal Sci,* 21:167-174.

National Institute of Agricultural Sciences, Japan. 1954. Insects and diseases of rice plants in Japan. Paper presented at the 4$^{th}$ session, International Rice Commission, Tokyo, 33 p.

Ou, S. H. 1985. Rice Diseases. 2$^{nd}$ edition Commonwealth Mycological Institute, Kew, U.K. 380 p.

Padmanaban, S. Y. 1965. Estimating losses from rice blast in India. pp. 203-221. In Rice Blast Disease, John Hopkins Press, Baltimore, Md.

Rogers S. G., Klee H. J., Horsch R. B., Farley R. T. 1987. Improved vectors for plant transformation: Expression cassette vectors and new selectable markers. *Methods in Enzymol.* 153:253-277.

Roy, A. K. 1993. Sheath blight of rice in India. *Indian Phytopathology* 46:197-205.

Schiffer, M., Chang, C. H., and Stevens, F. J. 1992. The functions of tryptophan residues in membrane proteins. *Prot. Engin.* 5:213-214.

Shen, M., and Lin, J. Y. 1994. The economic impact of rice blast disease in China. pp. 321-331. In Rice Blast Disease. R. S. Zeiglar, S. Leong, and P. S. Teng, eds. CAB International, Wallingford, U.K.

Sivamani, E., Shen, P., Opalka, N., Beachy, R. N., and Fauquet, C. M. 1996. Selection of large quantities of embryogenic calli from indica rice seeds for production of fertile transgenic plants using the biolistic method. *Plant Cell Reports* 15:322-327.

Smith, H. B. 1999. More than just a surface thing: Rice infection by *Magnaporthe grisea. Plant Cell* 11:1815-1817.

Song, W. -Y., Wang, G. -L., Chen, L. -L., Kim, H. -S., Pi, L. -Y., Holsten, T., Gardner, J., Wang, B., Zhai, W. -X., Zhu, L. -H., Fauquet, C. and Ronald, P. 1995. A receptor kinase-like protein encoded by the rice disease resistance gene, xa21. *Science* 270:1804-1806.

Symes, K. J. 1965. The inheritance of grain hardness in wheat as measured by the particle size index. *Aust. J. Agric. Res.* 16:113-123.

Terras, F. R. G., Schoofs, H. M. E., Thevissen, K., Osborn, R. W., Vanderleyden, J., Cammue, B. P. A., and Broekaert, W. F. 1993. Synergistic enhancement of the antifungal activity of wheat and barley thionins by radish and oilseed rape 2S albumins and by barley trypsin inhibitors. *Plant Physiol.* 103:1311-1319.

Tsai, W. H. 1970. Studies on the relation between rice blast disease. 1. Observations on the host range of rice sheath blight fungus, *Pellicularia sasakii* on weeds. *J. Taiwan Agric. Res.* 19:48-50.

Vasil, V., Srivastava, V., Castillo, A. M., Fromm, M. E., and Vasil, I. K. 1993. Rapid production of transgenic wheat plants by direct bombardment of cultured immature embryos. *Bio/Technology* 11:1553-1558.

Weeks, J. T., Anderson, O. D., and Blechl, A. E. 1993. Rapid production of multiple independent lines of fertile transgenic wheat (*Triticum aestivum*). *Plant Physiol.* 102:1077-1084.

Willets, D. A and Sherwood, J. E. 1999. Polymerase chain reaction detection of *Ustilago hordei* in leaves of susceptible and resistant barley varieties. *Phytopathology* 89:212-217.

---

We claim:

1. A transgenic plant cell, plant tissue or plant that comprises a construct comprising a nucleic acid sequence encoding puroindoline A.

2. The plant cell, plant tissue or plant of claim 1, wherein the nucleic acid sequence encoding puroindoline A is operably linked to a promoter.

3. The plant cell, plant tissue or plant of claim 1, wherein the plant is a grain plant.

4. The grain plant of claim 3, wherein the grain plant is selected from the group consisting of wheat, rice, maize, barley, sorghum, triticale and oats.

5. The plant cell, plant tissue or plant of claim 1, wherein the plant is a tomato plant.

6. The plant cell, plant tissue or plant of claim 1, wherein the nucleic acid sequence encoding puroindoline A is encoded by SEQ ID NO. 7.

7. A transgenic grain plant comprising a construct comprising a nucleic acid sequence encoding puroindoline A wherein the transgenic grain plant is capable of exhibiting a reduction in disease severity of greater than about 5% when compared to a corresponding non-transgenic grain plant following exposure of the transgenic grain plant and the corresponding non-transgenic grain plant to a fungus capable of damaging the plants.

8. The transgenic grain plant of claim 7, wherein the transgenic grain plant is capable of exhibiting a reduction in disease severity of between about 5% and about 10% when compared to the corresponding non-transgenic grain plant following exposure of the transgenic grain plant and the corresponding non-transgenic grain plant to a fungus capable of damaging the plants.

9. The transgenic grain plant of claim 7, wherein the transgenic grain plant is capable of exhibiting a reduction in disease severity of between about 10% and about 20% when compared to the corresponding non-transgenic grain plant following exposure of the transgenic grain plant and the corresponding non-transgenic grain plant to a fungus capable of damaging the plants.

10. The transgenic grain plant of claim 7, wherein the transgenic grain plant is capable of exhibiting a reduction in disease severity of between about 20% and about 30% when compared to the corresponding non-transgenic grain plant following exposure of the transgenic grain plant and the corresponding non-transgenic grain plant to a fungus capable of damaging the plants.

11. The transgenic grain plant of claim 7, wherein the transgenic grain plant is capable of exhibiting a reduction in disease severity of between about 30% and about 40% when compared to the corresponding non-transgenic grain plant following exposure of the transgenic grain plant and the corresponding non-transgenic grain plant to a fungus capable of damaging the plants.

12. The transgenic grain plant of claim 7, wherein the transgenic grain plant is capable of exhibiting a reduction in disease severity of between about 40% and about 50% when compared to the corresponding non-transgenic grain plant following exposure of the transgenic grain plant and the corresponding non-transgenic grain plant to a fungus capable of damaging the plants.

13. The transgenic grain plant of claim 7, wherein the transgenic grain plant is capable of exhibiting a reduction in disease severity of between about 50% and about 60% when compared to the corresponding non-transgenic grain plant following exposure of the transgenic grain plant and the corresponding non-transgenic grain plant to a fungus capable of damaging the plants.

14. The transgenic grain plant of claim 7, wherein the transgenic grain plant is capable of exhibiting a reduction in disease severity of between about 60% and about 70% when compared to the corresponding non-transgenic grain plant following exposure of the transgenic grain plant and the corresponding non-transgenic grain plant to a fungus capable of damaging the plants.

15. The transgenic grain plant of claim 7, wherein the transgenic grain plant is capable of exhibiting a reduction in disease severity of between about 70% and about 80% when compared to the corresponding non-transgenic grain plant following exposure of the transgenic grain plant and the corresponding non-transgenic grain plant to a fungus capable of damaging the plants.

16. A method of producing a transformed plant, wherein the method comprises introducing into a cell of a plant a nucleic acid encoding puroindoline A and regenerating a transformed plant from the transformed cell.

17. The method of claim 16, wherein the plant is a grain plant.

18. The method of claim 17, wherein the grain plant is selected from the group consisting of wheat, rice, maize, barley, sorghum, triticale and oats.

19. The method of claim 16, wherein the plant is a tomato plant.

20. A method of producing a transformed progeny plant, wherein the method comprises introducing into a cell of a plant a construct comprising a nucleic acid encoding puroindoline A; regenerating a transformed plant from the transformed cell; sexually crossing the regenerated transformed plant with a second plant of the same species, wherein the second plant is not transformed with a nucleic acid sequence encoding pumindo line A; harvesting the resultant seed; growing the harvested seed; and selecting a transformed progeny plant which comprises the construct.

21. The method of claim 20, wherein the plant is a grain plant.

22. The method of claim 21, wherein the gain plant is selected from the group consisting of wheat, rice, maize, barley, sorghum, triticale and oats.

23. The method of claim 20, wherein the plant is a tomato plant.

* * * * *

SEQUENCE LISTING

```
<160> NUMBER OF SEQ ID NOS: 10

<210> SEQ ID NO 1
<211> LENGTH: 35
<212> TYPE: DNA
<213> ORGANISM: Artificial sequence
<220> FEATURE:
<223> OTHER INFORMATION: RT-PCR Primer

<400> SEQUENCE: 1
cgggatccaa caatgaaggc cctcttcctc atagg                           35

<210> SEQ ID NO 2
<211> LENGTH: 35
<212> TYPE: DNA
<213> ORGANISM: Artificial sequence
<220> FEATURE:
<223> OTHER INFORMATION: RT-PCR Primer

<400> SEQUENCE: 2
```

```
ggatcccgcc agtaatagcc aatagtgccg gggat                              35

<210> SEQ ID NO 3
<211> LENGTH: 35
<212> TYPE: DNA
<213> ORGANISM: Artificial sequence
<220> FEATURE:
<223> OTHER INFORMATION: RT-PCR Primer

<400> SEQUENCE: 3
cgggatccaa caatgaagac cttattcctc ctagc                              35

<210> SEQ ID NO 4
<211> LENGTH: 32
<212> TYPE: DNA
<213> ORGANISM: Artificial sequence
<220> FEATURE:
<223> OTHER INFORMATION: RT-PCR Primer

<400> SEQUENCE: 4
ggatcccgcc agtaatagcc actagggaac tt                                 32

<210> SEQ ID NO 5
<211> LENGTH: 598
<212> TYPE: DNA
<213> ORGANISM: Triticum aestivum
<220> FEATURE:
<221> NAME/KEY: CDS
<222> LOCATION: (17)..(463)
<223> OTHER INFORMATION:

<400> SEQUENCE: 5
aaacaacatt gaaaac atg aag acc tta ttc ctc cta gct ctc ctt gct ctt   52
               Met Lys Thr Leu Phe Leu Leu Ala Leu Leu Ala Leu
                 1               5                  10 gta gcg agc aca acc ttc gcg caa tac tca gaa gtt ggc ggc tgg tac   100
Val Ala Ser Thr Thr Phe Ala Gln Tyr Ser Glu Val Gly Gly Trp Tyr
         15                  20                  25 aat gaa gtt ggc gga gga ggt ggt tct caa caa tgt ccg cag gag cgg   148
Asn Glu Val Gly Gly Gly Gly Gly Ser Gln Gln Cys Pro Gln Glu Arg
     30                  35                  40 ccg aag cta agc tct tgc aag gat tac gtg atg gag cga tgt ttc aca   196
Pro Lys Leu Ser Ser Cys Lys Asp Tyr Val Met Glu Arg Cys Phe Thr
 45                  50                  55                  60 atg aag gat ttt cca gtc acc tgg ccc aca aaa tgg tgg aag ggc ggc   244
Met Lys Asp Phe Pro Val Thr Trp Pro Thr Lys Trp Trp Lys Gly Gly
                 65                  70                  75 tgt gag cat gag gtt cgg gag aag tgc tgc aag cag ctg agc cag ata   292
Cys Glu His Glu Val Arg Glu Lys Cys Cys Lys Gln Leu Ser Gln Ile
             80                  85                  90 gca cca caa tgt cgc tgt gat tct atc cgg cga gtg atc caa ggc agg   340
Ala Pro Gln Cys Arg Cys Asp Ser Ile Arg Arg Val Ile Gln Gly Arg
         95                 100                 105 ctc ggt ggc ttc ttg ggc att tgg cga ggt gag gta ttc aaa caa ctt   388
Leu Gly Gly Phe Leu Gly Ile Trp Arg Gly Glu Val Phe Lys Gln Leu
    110                 115                 120 cag agg gcc cag agc ctc ccc tca aag tgc aac atg ggc gcc gac tgc   436
Gln Arg Ala Gln Ser Leu Pro Ser Lys Cys Asn Met Gly Ala Asp Cys
125                 130                 135                 140 aag ttc cct agt ggc tat tac tgg tga tgatatagcc tctattcgtg          483
Lys Phe Pro Ser Gly Tyr Tyr Trp
                145
```

```
ccaataaaat gtcacatatc atagcaagtg gcaaataaga gtgctgagtg atgatctatg      543
aataaaatca cccttgtata ttgatctgtg ttcgagaaaa aaaaaaaaaa aaaaa           598

<210> SEQ ID NO 6
<211> LENGTH: 148
<212> TYPE: PRT
<213> ORGANISM: Triticum aestivum

<400> SEQUENCE: 6

Met Lys Thr Leu Phe Leu Leu Ala Leu Leu Ala Leu Val Ala Ser Thr
1               5                   10                  15

Thr Phe Ala Gln Tyr Ser Glu Val Gly Gly Trp Tyr Asn Glu Val Gly
            20                  25                  30

Gly Gly Gly Ser Gln Gln Cys Pro Gln Glu Arg Pro Lys Leu Ser
        35                  40                  45

Ser Cys Lys Asp Tyr Val Met Glu Arg Cys Phe Thr Met Lys Asp Phe
    50                  55                  60

Pro Val Thr Trp Pro Thr Lys Trp Trp Lys Gly Gly Cys Glu His Glu
65                  70                  75                  80

Val Arg Glu Lys Cys Cys Lys Gln Leu Ser Gln Ile Ala Pro Gln Cys
                85                  90                  95

Arg Cys Asp Ser Ile Arg Arg Val Ile Gln Gly Arg Leu Gly Gly Phe
            100                 105                 110

Leu Gly Ile Trp Arg Gly Glu Val Phe Lys Gln Leu Gln Arg Ala Gln
        115                 120                 125

Ser Leu Pro Ser Lys Cys Asn Met Gly Ala Asp Cys Lys Phe Pro Ser
    130                 135                 140

Gly Tyr Tyr Trp
145

<210> SEQ ID NO 7
<211> LENGTH: 680
<212> TYPE: DNA
<213> ORGANISM: Triticum aestivum
<220> FEATURE:
<221> NAME/KEY: CDS
<222> LOCATION: (25)..(471)
<223> OTHER INFORMATION:

<400> SEQUENCE: 7
cctgcaccaa aacacactga caac atg aag gcc ctc ttc ctc ata gga ctg        51
                          Met Lys Ala Leu Phe Leu Ile Gly Leu
                          1               5 ctt gct ctg gta gcg agc acc gcc ttt gcg caa tat agc gaa gtt gtt        99
Leu Ala Leu Val Ala Ser Thr Ala Phe Ala Gln Tyr Ser Glu Val Val
10                  15                  20                  25 ggc agt tac gat gtt gct ggc ggg ggt ggt gct caa caa tgc cct gta       147
Gly Ser Tyr Asp Val Ala Gly Gly Gly Gly Ala Gln Gln Cys Pro Val
                30                  35                  40 gag aca aag cta aat tca tgc agg aat tac ctg cta gat cga tgc tca       195
Glu Thr Lys Leu Asn Ser Cys Arg Asn Tyr Leu Leu Asp Arg Cys Ser
            45                  50                  55 acg atg aag gat ttc ccg gtc acc tgg cgt tgg tgg aaa tgg tgg aag       243
Thr Met Lys Asp Phe Pro Val Thr Trp Arg Trp Trp Lys Trp Trp Lys
        60                  65                  70 gga ggt tgt caa gag ctc ctt ggg gag tgt tgc agt cgg ctc ggc caa       291
Gly Gly Cys Gln Glu Leu Leu Gly Glu Cys Cys Ser Arg Leu Gly Gln
    75                  80                  85 atg cca ccg caa tgc cgc tgc aac atc atc cag ggg tca atc caa ggc       339
```

```
Met Pro Pro Gln Cys Arg Cys Asn Ile Ile Gln Gly Ser Ile Gln Gly
 90                  95                 100                105 gat ctc

```
                5                   10                  15                  20
tat agc gaa gtt gtt ggc agt tac gat gtt gct ggc ggg ggt ggt gct           150
Tyr Ser Glu Val Val Gly Ser Tyr Asp Val Ala Gly Gly Gly Gly Ala
                    25                  30                  35 caa caa tgc cct gta gag aca aag cta aat tca tgc agg aat tac ctg           198
Gln Gln Cys Pro Val Glu Thr Lys Leu Asn Ser Cys Arg Asn Tyr Leu
            40                  45                  50 cta gat cga tgc tca acg atg aag gat ttc ccg gtc acc tgg cgt tgg           246
Leu Asp Arg Cys Ser Thr Met Lys Asp Phe Pro Val Thr Trp Arg Trp
                55                  60                  65 tgg aaa tgg tgg aag gga ggt tgt caa gag ctc ctt ggg gag tgt tgc           294
Trp Lys Trp Trp Lys Gly Gly Cys Gln Glu Leu Leu Gly Glu Cys Cys
        70                  75                  80 agt cgg ctc ggc caa atg cca ccg caa tgc cgc tgc aac atc atc cag           342
Ser Arg Leu Gly Gln Met Pro Pro Gln Cys Arg Cys Asn Ile Ile Gln
85                  90                  95                  100 ggg tca atc caa ggc gat ctc ggt ggc atc ttc gga ttt cag cgt gat           390
Gly Ser Ile Gln Gly Asp Leu Gly Gly Ile Phe Gly Phe Gln Arg Asp
                    105                 110                 115 cgg gca agc aaa gtg ata caa gaa gcc aag aac ctg ccg ccc agg tgc           438
Arg Ala Ser Lys Val Ile Gln Glu Ala Lys Asn Leu Pro Pro Arg Cys
            120                 125                 130 aac cag ggc cct ccc tgc aac atc ccc ggc act att ggc tat tac tgg           486
Asn Gln Gly Pro Pro Cys Asn Ile Pro Gly Thr Ile Gly Tyr Tyr Trp
                135                 140                 145 tga tgtagcttcc atttatgact agctaataaa ctgtcacata ccactgcgtg                539
tgacaaataa aagtggtcat ggaataattt atgaataaaa tttcagcatg tgcctgcgcg         599
aggtgtctat agcaaaaaaa aaaaaaaaaa aa                                       631

<210> SEQ ID NO 10
<211> LENGTH: 148
<212> TYPE: PRT
<213> ORGANISM: Triticum aestivum

<400> SEQUENCE: 10

Met Lys Ala Leu Phe Leu Ile Gly Leu Leu Ala Leu Val Ala Ser Thr
1               5                   10                  15

Ala Phe Ala Gln Tyr Ser Glu Val Val Gly Ser Tyr Asp Val Ala Gly
            20                  25                  30

Gly Gly Gly Ala Gln Gln Cys Pro Val Glu Thr Lys Leu Asn Ser Cys
        35                  40                  45

Arg Asn Tyr Leu Leu Asp Arg Cys Ser Thr Met Lys Asp Phe Pro Val
    50                  55                  60

Thr Trp Arg Trp Trp Lys Trp Trp Lys Gly Gly Cys Gln Glu Leu Leu
65                  70                  75                  80

Gly Glu Cys Cys Ser Arg Leu Gly Gln Met Pro Pro Gln Cys Arg Cys
                85                  90                  95

Asn Ile Ile Gln Gly Ser Ile Gln Gly Asp Leu Gly Gly Ile Phe Gly
            100                 105                 110

Phe Gln Arg Asp Arg Ala Ser Lys Val Ile Gln Glu Ala Lys Asn Leu
        115                 120                 125

Pro Pro Arg Cys Asn Gln Gly Pro Pro Cys Asn Ile Pro Gly Thr Ile
    130                 135                 140

Gly Tyr Tyr Trp
145
```